United States Patent
Owens et al.

(10) Patent No.: US 12,303,718 B2
(45) Date of Patent: May 20, 2025

(54) GRAPHICAL REPRESENTATION OF RADIATION THERAPY

(71) Applicant: RefleXion Medical, Inc., Hayward, CA (US)

(72) Inventors: Michael Kirk Owens, San Francisco, CA (US); Peter Demetri Olcott, Los Gatos, CA (US); Rostem Bassalow, Lacey, WA (US)

(73) Assignee: RefleXion Medical, Inc., Hayward, CA (US)

( * ) Notice: Subject to any disclaimer, the term of this patent is extended or adjusted under 35 U.S.C. 154(b) by 11 days.

(21) Appl. No.: 17/479,873

(22) Filed: Sep. 20, 2021

(65) Prior Publication Data
US 2022/0001209 A1      Jan. 6, 2022

Related U.S. Application Data

(63) Continuation of application No. 16/582,308, filed on Sep. 25, 2019, now abandoned, which is a
(Continued)

(51) Int. Cl.
*A61N 5/10* (2006.01)
*A61B 6/03* (2006.01)
*A61B 6/46* (2024.01)

(52) U.S. Cl.
CPC ............ *A61N 5/1071* (2013.01); *A61B 6/032* (2013.01); *A61B 6/463* (2013.01); *A61N 5/1045* (2013.01);
(Continued)

(58) Field of Classification Search
CPC .. A61N 5/1071; A61N 5/1048; A61N 5/1081; A61N 5/1067; A61B 6/032; A61B 6/037
See application file for complete search history.

(56) References Cited

U.S. PATENT DOCUMENTS

| 3,794,840 A | 2/1974 | Scott |
| 6,385,286 B1 | 5/2002 | Fitchard et al. |
| (Continued) | | |

FOREIGN PATENT DOCUMENTS

| CN | 1824342 A | 8/2006 |
| CN | 101267767 A | 9/2008 |
| (Continued) | | |

OTHER PUBLICATIONS

Adaptive Radiation Therapy: ISBN:9781439816356. 2011. CRC Press. X Allen Li (Ed.): 426 pages (cover only); URL: https://www.google.com/books/edition/Adaptive_Radiation_Therapy/9hEPvAlgPfMC (accessed Aug. 31, 2021).
(Continued)

*Primary Examiner* — Sean M Luck
(74) *Attorney, Agent, or Firm* — Cooley LLP

(57) ABSTRACT

Described herein are methods for monitoring the radiation delivery during a radiotherapy delivery session and providing a graphical representation of radiation delivery to an operator (e.g., a clinician, a medical physicist, a radiation therapy technologist). The graphics are updated in real-time, as radiation data is collected by the radiotherapy system, and in some variations, can be updated every 15 minutes or less. A variety of graphical representations ("graphics") can be used to indicate the status of radiation delivery relative to the planned radiation delivery. Methods optionally include calculating a range of acceptable metric values, generating graphics that represent the range of acceptable metrics values, and generating a graphic that depicts the real-time values of those metrics overlaid with the range of acceptable metrics values.

17 Claims, 20 Drawing Sheets

Related U.S. Application Data continuation of application No. 16/046,746, filed on Jul. 26, 2018, now Pat. No. 10,456,600.

(60) Provisional application No. 62/537,422, filed on Jul. 26, 2017.

(52) U.S. Cl.
CPC ............ *A61N 5/1081* (2013.01); *A61B 6/037* (2013.01); *A61N 5/1067* (2013.01); *A61N 2005/1074* (2013.01); *A61N 2005/1076* (2013.01)

(56) References Cited

U.S. PATENT DOCUMENTS

| | | |
|---|---|---|
| 6,438,202 B1 | 8/2002 | Olivera et al. |
| 6,618,467 B1 | 9/2003 | Ruchala et al. |
| 6,810,108 B2 | 10/2004 | Clark et al. |
| 7,265,356 B2 | 9/2007 | Pelizzari et al. |
| 7,280,633 B2 | 10/2007 | Cheng et al. |
| 7,302,033 B2 | 11/2007 | Carrano et al. |
| 7,379,531 B2 | 5/2008 | Esham et al. |
| 7,412,029 B2 | 8/2008 | Myles |
| 7,412,280 B2 | 8/2008 | Hertel et al. |
| 7,446,328 B2 | 11/2008 | Rigney et al. |
| 7,469,035 B2 | 12/2008 | Keall et al. |
| 7,522,779 B2 | 4/2009 | Fu et al. |
| 7,623,623 B2 | 11/2009 | Raanes et al. |
| 7,639,853 B2 | 12/2009 | Olivera et al. |
| 7,831,289 B2 | 11/2010 | Riker et al. |
| 7,839,972 B2 | 11/2010 | Ruchala et al. |
| 7,906,770 B2 | 3/2011 | Otto |
| 7,945,021 B2 | 5/2011 | Shapiro et al. |
| 7,983,380 B2 | 7/2011 | Guertin et al. |
| 8,019,042 B2 | 9/2011 | Shukla et al. |
| 8,063,376 B2 | 11/2011 | Maniawski et al. |
| 8,086,004 B2 | 12/2011 | Kuduvalli et al. |
| 8,090,074 B2 | 1/2012 | Filiberti et al. |
| 8,107,589 B2 | 1/2012 | Sakurai et al. |
| 8,144,962 B2 | 3/2012 | Busch et al. |
| 8,149,991 B2 | 4/2012 | Moreau |
| 8,269,195 B2 | 9/2012 | Rigney et al. |
| 8,278,633 B2 | 10/2012 | Nord et al. |
| 8,295,430 B2 | 10/2012 | Zhu et al. |
| 8,331,532 B2 | 12/2012 | Nord et al. |
| 8,406,844 B2 | 3/2013 | Ruchala et al. |
| 8,442,287 B2 | 5/2013 | Fordyce, II et al. |
| 8,457,372 B2 | 6/2013 | Fu et al. |
| 8,467,497 B2 | 6/2013 | Lu et al. |
| 8,483,803 B2 | 7/2013 | Partain et al. |
| 8,509,383 B2 | 8/2013 | Lu et al. |
| 8,536,547 B2 | 9/2013 | Maurer, Jr. et al. |
| 8,554,573 B2 | 10/2013 | Pekar et al. |
| 8,559,596 B2 | 10/2013 | Thomson et al. |
| 8,588,367 B2 | 11/2013 | Busch et al. |
| 8,605,857 B1 | 12/2013 | Renner |
| 8,681,938 B2 | 3/2014 | Myles |
| 8,767,917 B2 | 7/2014 | Ruchala et al. |
| 8,816,307 B2 | 8/2014 | Kuusela et al. |
| 8,824,630 B2 | 9/2014 | Maurer, Jr. et al. |
| 8,831,706 B2 | 9/2014 | Fu et al. |
| 8,836,697 B2 | 9/2014 | Nord et al. |
| 8,861,672 B2 | 10/2014 | Maltz et al. |
| 8,874,187 B2 | 10/2014 | Thomson et al. |
| 8,917,813 B2 | 12/2014 | Maurer, Jr. et al. |
| 9,019,307 B1 | 4/2015 | Grimm |
| 9,155,909 B2 | 10/2015 | Ishikawa |
| 9,437,340 B2 | 9/2016 | Echner et al. |
| 9,498,167 B2 | 11/2016 | Mostafavi et al. |
| 9,539,441 B2 | 1/2017 | Lane et al. |
| 9,616,251 B2 | 4/2017 | Filiberti et al. |
| 9,849,308 B2 | 12/2017 | Berlinger et al. |
| 9,956,429 B2 | 5/2018 | Holmes et al. |
| 9,974,494 B2 | 5/2018 | Mostafavi et al. |
| 9,987,504 B2 | 6/2018 | Nord et al. |
| 9,990,711 B2 | 6/2018 | Lugosi et al. |
| 10,065,049 B2 | 9/2018 | Lugosi et al. |
| 10,279,196 B2 | 5/2019 | West et al. |
| 10,449,389 B2 | 10/2019 | Ollila et al. |
| 10,456,600 B2 | 10/2019 | Owens et al. |
| 10,674,983 B2 | 6/2020 | Black |
| 10,688,320 B2 | 6/2020 | Voronenko et al. |
| 10,737,118 B2 | 8/2020 | Mostafavi |
| 10,799,716 B2 | 10/2020 | Morgas et al. |
| 10,806,368 B2 | 10/2020 | Hebert |
| 10,835,761 B2 | 11/2020 | Beriault et al. |
| 10,918,885 B2 | 2/2021 | Haas et al. |
| 11,033,757 B2 | 6/2021 | Voronenko et al. |
| 11,083,913 B2 | 8/2021 | Lachaine et al. |
| 11,154,269 B2 | 10/2021 | Shea et al. |
| 11,173,324 B2 | 11/2021 | Paysan et al. |
| 11,278,737 B2 | 3/2022 | Peltola et al. |
| 11,291,858 B2 | 4/2022 | MacDonald et al. |
| 11,358,008 B2 | 6/2022 | Voronenko et al. |
| 11,369,805 B2 | 6/2022 | Maltz |
| 11,369,806 B2 | 6/2022 | Laurence, Jr. et al. |
| 11,478,662 B2 | 10/2022 | Sayeh et al. |
| 11,504,548 B2 | 11/2022 | Fong de los Santos et al. |
| 11,504,550 B2 | 11/2022 | Maolinbay |
| 11,596,807 B2 | 3/2023 | Maurer et al. |
| 11,617,903 B2 | 4/2023 | Lamb et al. |
| 11,633,626 B2 | 4/2023 | Voronenko et al. |
| 11,648,418 B2 | 5/2023 | Owens et al. |
| 11,684,801 B2 | 6/2023 | Schadewaldt et al. |
| 11,896,848 B2 | 2/2024 | Janardhanan et al. |
| 12,115,386 B2 | 10/2024 | Voronenko et al. |
| 2002/0137991 A1 | 9/2002 | Scarantino et al. |
| 2004/0079899 A1 | 4/2004 | Ma |
| 2004/0122308 A1 | 6/2004 | Ding |
| 2005/0207531 A1 | 9/2005 | Dempsey et al. |
| 2006/0159220 A1 | 7/2006 | Heuscher |
| 2006/0173294 A1 | 8/2006 | Ein-Gal |
| 2007/0025524 A1 | 2/2007 | Yue |
| 2008/0071131 A1 | 3/2008 | Rietzel |
| 2008/0226030 A1* | 9/2008 | Otto .................... A61N 5/1031 378/65 |
| 2009/0116616 A1 | 5/2009 | Lu et al. |
| 2009/0117044 A1 | 5/2009 | Hengerer et al. |
| 2010/0054411 A1 | 3/2010 | Nord et al. |
| 2010/0086183 A1 | 4/2010 | Vik et al. |
| 2010/0150309 A1 | 6/2010 | Nord et al. |
| 2011/0049377 A1 | 3/2011 | Morf et al. |
| 2011/0122997 A1 | 5/2011 | Lu et al. |
| 2011/0163238 A1 | 7/2011 | Teshigawara et al. |
| 2011/0200170 A1 | 8/2011 | Nord et al. |
| 2011/0291015 A1 | 12/2011 | Mazin |
| 2012/0053961 A1 | 3/2012 | Wang et al. |
| 2012/0230464 A1 | 9/2012 | Ling et al. |
| 2012/0250971 A1 | 10/2012 | Holmes et al. |
| 2012/0292534 A1 | 11/2012 | Geneser et al. |
| 2013/0083004 A1 | 4/2013 | Nord et al. |
| 2013/0188856 A1 | 7/2013 | Adler, Jr. et al. |
| 2014/0005464 A1 | 1/2014 | Bharat et al. |
| 2014/0031603 A1 | 1/2014 | Robar et al. |
| 2014/0126700 A1 | 5/2014 | Gertner et al. |
| 2014/0252227 A1 | 9/2014 | Sasai et al. |
| 2014/0270053 A1 | 9/2014 | Larson |
| 2014/0275704 A1* | 9/2014 | Zhang .................. A61N 5/1067 600/1 |
| 2014/0336438 A1 | 11/2014 | Bharat et al. |
| 2015/0043709 A1 | 2/2015 | Shapiro et al. |
| 2015/0161338 A1 | 6/2015 | Scherrer et al. |
| 2015/0224342 A1 | 8/2015 | Baltes et al. |
| 2015/0251017 A1 | 9/2015 | De Crevoisier et al. |
| 2015/0360056 A1 | 12/2015 | Xing et al. |
| 2015/0367143 A1 | 12/2015 | Muraki et al. |
| 2016/0023019 A1 | 1/2016 | Filiberti et al. |
| 2016/0038767 A1 | 2/2016 | Wiersma et al. |
| 2016/0074541 A1 | 3/2016 | Zalutsky et al. |
| 2016/0140300 A1 | 5/2016 | Purdie et al. |
| 2016/0193480 A1 | 7/2016 | Ribbing et al. |
| 2016/0287906 A1 | 10/2016 | Nord et al. |
| 2016/0361566 A1 | 12/2016 | Larkin et al. |

(56) References Cited

U.S. PATENT DOCUMENTS

| | | |
|---|---|---|
| 2016/0361568 A1 | 12/2016 | Chappelow et al. |
| 2017/0014642 A1 | 1/2017 | An et al. |
| 2017/0023494 A1 | 1/2017 | Yu et al. |
| 2017/0028220 A1 | 2/2017 | Schulte et al. |
| 2017/0087385 A1 | 3/2017 | Miettinen et al. |
| 2017/0095678 A1 | 4/2017 | Oster et al. |
| 2017/0209715 A1 | 7/2017 | Ruebel et al. |
| 2018/0133518 A1 | 5/2018 | Harper et al. |
| 2018/0154179 A1 | 6/2018 | Ollila et al. |
| 2018/0345042 A1 | 12/2018 | Voronenko et al. |
| 2018/0369611 A1 | 12/2018 | Owens et al. |
| 2019/0001152 A1 | 1/2019 | O'Connor et al. |
| 2019/0054315 A1 | 2/2019 | Isola et al. |
| 2019/0070436 A1 | 3/2019 | Willcut et al. |
| 2020/0121953 A1 | 4/2020 | Fredriksson |
| 2021/0236854 A1 | 8/2021 | Voronenko et al. |
| 2021/0339047 A1 | 11/2021 | Janardhanan et al. |
| 2022/0001209 A1 | 1/2022 | Owens et al. |
| 2022/0126117 A1 | 4/2022 | Voronenko et al. |
| 2023/0356003 A1 | 11/2023 | Voronenko et al. |
| 2023/0390580 A1 | 12/2023 | Owens et al. |
| 2024/0316363 A1 | 9/2024 | Voronenko et al. |

FOREIGN PATENT DOCUMENTS

| | | |
|---|---|---|
| CN | 101489477 A | 7/2009 |
| CN | 101496018 A | 7/2009 |
| CN | 102068763 A | 5/2011 |
| CN | 102641561 A | 8/2012 |
| CN | 103180014 A | 6/2013 |
| CN | 103209736 A | 7/2013 |
| CN | 103845068 A | 6/2014 |
| CN | 104284697 A | 1/2015 |
| CN | 105658279 A | 6/2016 |
| CN | 106563211 A | 4/2017 |
| CN | 107072595 A | 8/2017 |
| CN | 107072628 A | 8/2017 |
| EP | 2 072 081 A1 | 6/2009 |
| EP | 1 501 604 B1 | 12/2009 |
| EP | 1 898 234 B1 | 4/2010 |
| EP | 2 904 974 A1 | 8/2015 |
| EP | 2 990 078 A1 | 3/2016 |
| EP | 2 874 702 B1 | 9/2016 |
| JP | 2009-160308 A | 7/2009 |
| JP | 2009-538195 A | 11/2009 |
| JP | 2012-035072 A | 2/2012 |
| JP | 2012-506734 A | 3/2012 |
| JP | 2013-059576 A | 4/2013 |
| JP | 2014-023741 A | 2/2014 |
| JP | 2014-503315 A | 2/2014 |
| JP | 2016-055161 A | 4/2016 |
| JP | 2016-168077 A | 9/2016 |
| WO | WO-00/59576 A1 | 10/2000 |
| WO | WO-2007/082126 A2 | 7/2007 |
| WO | WO-2007/082126 A3 | 7/2007 |
| WO | WO-2008/011725 A1 | 1/2008 |
| WO | WO-2008/013598 A2 | 1/2008 |
| WO | WO-2008/013598 A3 | 1/2008 |
| WO | WO-2013/024380 A1 | 2/2013 |
| WO | WO-2013/054788 A1 | 4/2013 |
| WO | WO-2013/093852 A1 | 6/2013 |
| WO | WO-2016/023786 A1 | 2/2016 |
| WO | WO-2016/064750 A1 | 4/2016 |
| WO | WO-2017/081768 A1 | 5/2017 |
| WO | WO-2018/183748 A1 | 10/2018 |
| WO | WO-2018/222751 A1 | 12/2018 |
| WO | WO-2018/237328 A1 | 12/2018 |
| WO | WO-2019/160958 A1 | 8/2019 |

OTHER PUBLICATIONS

Akpati, H.C. et al. (2008). "Unified dosimetry index (UDI): A figure of merit for ranking treatment plans," J Appl Clin Med Phys. 9:99-108.

Alrowaili, Z.A. et al. (2015). "2D mapping of the MV photon fluence and 3D dose reconstruction in real itime for quality assurance during radiotherapy treatment," J. Instrumentation IOP Science 10:P09019, 17 total pages.

ArcCHECK® & 3DVH (2016). Sun Nuclear, located at https://www.sunnuclear.com/solutions/patientqa/arccheck3dvh, retrieved on Jul. 31, 2019, 12 total pages.

Chang, J.Y. et al. (2008). "Image-guided radiation therapy for non-small cell lung cancer," J. Thorac Oncol. 3:177-186 (Abstract Only).

Chen, Q. et al. (2016). "SU-D-201-03: During-Treatment Delivery Monitoring System for TomoTherapy," Med. Phys. 43:3334, 1 total page.

Chen, Q. (2016) "During treatment delivery monitoring system for tomotherapy," Presentation, University of Virginia Health System, 16 total pages.

Chen, X. et al. (2012). "Smoothing proximal gradient method for general structured sparse regression," The Annals of Applied Statistics 6:719-752.

Croteau, E. et al. (2016). "PET Metabolic Biomarkers for Cancer," Biomark Cancer. 8(Suppl 2):61-69.

Dieterich, S. et al. (2003). "Skin respiratory motion tracking for stereotactic radiosurgery using the CyberKnife," Elsevier Int'l Congress Series 1256:130-136.

ECN Magazine (2016). "Magic plate radiation detector helps improve cancer radiotherapy," located at https://www.ecnmag.com/news/2016/03/magic-plate-radiation-detector-helps-improve-cancer-radiotherapy, retrieved on Jul. 31, 2019, 5 total pages.

Extended European Search Report mailed on Feb. 3, 2021, for EP Application No. 18 810 297.4, filed on May 30, 2018, 4 pages.

Extended European Search Report mailed on Mar. 15, 2021, for EP Application No. 18 837.615.6, filed on Jul. 26, 2018, 8 pages.

Extended European Search Report mailed on Jun. 14, 2021, for EP Application No. 18 821 003.3, filed on Jun. 22, 2018, 5 pages.

Fan, Q. et al. (2013). "Toward a Planning Scheme for Emission Guided Radiation Therapy (EGRT): FDG Based Tumor Tracking in a Metastatic Breast Cancer Patient," Med. Phys. 40(8): 12 pages.

Fan, Q. et al. (2012). "Emission Guided Radiation Therapy for Lung and Prostrate Cancers: A Feasibility Study on a Digital Patient," Med. Phys. 39(11):7140-7152.

Final Office Action mailed on Jul. 14, 2021, for U.S. Appl. No. 16/582,308, filed Sep. 25, 2019, 8 pages.

Final Office Action mailed on May 18, 2022, for U.S. Appl. No. 16/016,272, filed Jun. 22, 2018, 31 pages.

Final Office Action mailed on Sep. 15, 2022, for U.S. Appl. No. 16/582,308, filed Sep. 25, 2019, 10 pages.

Fredriksson (2013). "Robust optimization of radiation therapy accounting for geometric uncertainty," KTH Engin. Sciences, pp. 8-14.

Gibbons, J.P. (2004). "Dose calculation and verification for tomotherapy," 2004 ACMP Meeting, Scottsdale, AZ., 71 total pages.

Handsfield, L.L. et al. (2014). "Phantomless patient-specific TomoTherapy QA via delivery performance monitoring and a secondary Monte Carlo dose calculation," Med. Phys. 41:101703-1-101703-9.

Hoeben, B.A.W. et al. (2013). "Molecular PET imaging for biology-guided adaptive radiotherapy of head and neck cancer," Acta Oncologica 52:1257-1271.

Hunt, M.A. et al. (2003). "Treatment Planning Considerations using IMRT," pp. 103-121.

International Search Report mailed on Nov. 16, 2018, for PCT Application No. PCT/US2018/039104, filed on Jun. 22, 2018, 4 pages.

International Search Report mailed on Oct. 3, 2018, for PCT Application No. PCT/US2018/035188, filed on May 30, 2018, 4 pages.

International Search Report mailed on Oct. 3, 2018, for PCT Application No. PCT/US2018/043954, filed on Jul. 26, 2018, 3 pages.

International Search Report mailed on Apr. 23, 2020, for PCT Application No. PCT/US2020/013927, filed on Jan. 16, 2020, 3 pages.

(56) References Cited

OTHER PUBLICATIONS

International Search Report mailed on Dec. 1, 2020, for PCT Application No. PCT/US2020/040774, filed on Jul. 2, 2020, 4 pages.
Kak, A. et al. (1988). "Aliasing artifacts and noise in CT images," Principles of computerized tomographic imaging, pp. 177-201.
Kapatoes, J.M. et al. (2001). "A feasible method for clinical delivery verification and dose reconstruction in tomotherapy," *Med. Phys.* 28:528-542.
Kapatoes, J. M. (2001). "On the accuracy and effectiveness of dose reconstruction for tomotherapy," *Physics in Med. Biol.* 46:943-966.
Keall, P.J. et al. (2001). "Motion adaptive x-ray therapy: a feasibility study," *Physics in Med. Biol.* 46:1-10.
Kim et al. "18F-FDG PET/CT of Advanced Gastric Carcinoma and Association of H ER2 Expression with Standardized Uptake Value." Asia Oceania J Nucl Med Biol, 2014; 2(1): 12-18.
Kong et al. "Effect of Midtreatment PET/CT-Adapted Radiation Therapy With Concurrent Chemotherapy in Patients With Locally Advanced Non-Small-Cell Lung Cancer." JAMA Oncol. Oct. 2017; 3(10): 1358-1365. Published online Oct. 12, 2017. Prepublished online Jun. 1, 2017.
Lu, W. (2008). "Real-time motion-adaptive delivery (MAD) using binary MLC: I. Static beam (topotherapy) delivery," Phys. Med. Biol. 53:6491-6511.
Lu, W. (2009). "Real-time motion-adaptive-optimization (MAO) in tomotherapy," Phys. Med. Biol. 54:4373-4398.
Mackie, T.R. et al. (1993). "Tomotherapy: A new concept for the delivery of dynamic conformal radiotherapy," Med. Phys. 20:1709-1719.
Mazin, S.R. et al. (2010). "Emission-guided radiation therapy: Biologic targeting and adaptive treatment," Am. College of Radiology, pp. 989-990.
McMahon, R. et al. (2008). "A real-time dynamic-MLC control algorithm for delivering IMRT to targets undergoing 2D rigid motion in the beam's eye view," Med. Phys. 35:3875-3888.
Non-Final Office Action mailed on Dec. 6, 2019, for U.S. Appl. No. 15/993,325, filed May 30, 2018, 8 pages.
Non-Final Office Action mailed on Dec. 22, 2020, for U.S. Appl. No. 16/554,258, filed Aug. 28, 2019, 11 pages.
Non-Final Office Action mailed on Feb. 11, 2021, for U.S. Appl. No. 16/582,308, filed Sep. 25, 2019, 9 pages.
Non-Final Office Action mailed on Sep. 21, 2021, for U.S. Appl. No. 16/016,272, filed Jun. 22, 2018, 34 pages,.
Non-Final Office Action mailed on Jun. 8, 2022, for U.S. Appl. No. 16/582,308, filed Sep. 25, 2019, 9 pages.
Non-Final Office Action mailed on Aug. 30, 2022, for U.S. Appl. No. 17/235,812, filed Apr. 20, 2021, 8 pages.
Notice of Allowance mailed on Jul. 25, 2019, for U.S. Appl. No. 16/046,746, filed Jul. 26, 2018, 8 pages.
Notice of Allowance mailed on Aug. 15, 2019, for U.S. Appl. No. 16/046,746, filed Jul. 26, 2018, 7 pages.
Notice of Allowance mailed on Apr. 20, 2020, for U.S. Appl. No. 15/993,325, filed May 30, 2018, 7 pages.
Olivera, G.H. et al. (2000). "Modifying a plan delivery without re-optimization to account for patient offset in tomotherapy," Proceedings of the 22$^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," *J. Cancer Sci. Ther.* 2:145-152.
Parodi, K. (2015). "Vision 20/20: Positron emission tomography in radiation therapy planning, delivery and monitoring," Am. Assoc. Phys. Med. 42:7153-7168.
Pyakuryal, A. et al. (2010). "A computational tool for the efficient analysis of dose-volume histograms for radiation therapy treatment plans," J Appl. Clin. Med. Phys. 11:137-157.
Rahmim, A. et al. (2009). "Four-dimensional (4d) image reconstruction strategies in dynamic pet: beyond conventional independent frame reconstruction," Medical physics 36:3654-3670.

Reader, A.J. et al. (2007). "Advances in pet image reconstruction," PET clinics 2:173-190.
Riederer, S.J. et al. (1978). "The noise power spectrum in computed x-ray tomography," Physics in medicine and biology 23:446.
ScandiDos (2019). Delta$^4$ located at https://delta4family.com/products, retrieved on Jul. 31, 2019, 5 total pages.
Seppenwoolde, Y. et al. (2002). "Precise and real-time measurement of 3d tumor motion in lung due to breathing and heartbeat, measured during radiotherapy," International Journal of Radiation Oncology Biology Physics 53:822-834.
Thorek, D. "Positron lymphography: multimodal, high-resolution, dynamic mapping and resection of lymph nodes after X intradermal injection of 18F-FDG." J Nucl Med. Sep. 2012;53(9):1438-45.
Thorwarth, D. et al. (2010). "Physical radiotherapy treatment planning based on functional PET/CT data," Radiotherapy Oncology, pp. 317-324.
Tuncel, N. "Adaptive radiotherapy from past to future frontiers." International Journal of Radiology & Radiation Therapy 2021; 8(2):81-84.
Varian Medical Systems (2019). MOBIUS3D, Varian oncology software products, located at https://www.varian.com/oncology/products/software/mobius3d, retrieved on Jul. 31, 2019, 3 total pages.
Written Opinion of the International Searching Authority mailed on Nov. 16, 2018, for PCT Application No. PCT/US2018/039104, filed on Jun. 22, 2018, 6 pages.
Written Opinion of the International Searching Authority mailed on Oct. 3, 2018, for PCT Application No. PCT/US2018/035188, filed on May 30, 2018, 28 pages.
Written Opinion of the International Searching Authority mailed on Oct. 3, 2018, for PCT Application No. PCT/US2018/043954, filed on Jul. 26, 2018, 5 pages.
Written Opinion of the International Searching Authority mailed on Apr. 23, 2020, for PCT Application No. PCT/US2020/013927, filed on Jan. 16, 2020, 4 pages.
Written Opinion of the International Searching Authority mailed on Dec. 1, 2020, for PCT Application No. PCT/US2020/040774, filed on Jul. 2, 2020, 8 pages.
Written Opinion of the International Searching Authority mailed on Jun. 27, 2017, for PCT Patent Application No. PCT/US2017/021647, filed on Mar. 9, 2017, 5 pages.
Yan, D. et al. (1997). "Adaptive radiation therapy," *Physics Med. Biol.* 42:123-132.
Zhang, H. et al. (2002). Progress in the Physics of Tumor Radiation Therapy, Beijing Medical University, China Union Medical University Joint Press, p. 164 (with English translation).
Zhao, H. et al. (2015). Practical Imaging Diagnosis, University Press, Aug. 2015, p. 167 (with English translation).
Corrected Notice of Allowability mailed on Mar. 13, 2023, for U.S. Appl. No. 17/235,812, filed Apr. 20, 2021, 4 pages.
Extended European Search Report mailed on Jun. 23, 2023, for EP Application No. 20 840 804.7, filed on Jul. 2, 2020, 7 pages.
Guohua H. et al. (Nov. 2002). "Chapter 8: Radionuclide diagnosis and treatment," in *Bladder Tumor*, Shanghai: Tongji University Press, first edition, first printing, p. 41 (with English Translation).
Hongsheng, S. (Aug. 2015). "Chapter 8: Nuclear medicine imaging," in *Practical Imaging Diagnosis*, Xi'an Jiaotong University Press, first edition, first printing, p. 167 (with English Translation).
Non-Final Office Action mailed on Nov. 21, 2022, for U.S. Appl. No. 16/016,272, filed Jun. 22, 2018, 27 pages.
Notice of Allowance mailed on Feb. 1, 2023, for U.S. Appl. No. 17/235,812, filed Apr. 20, 2021, 7 pages.
Notice of Allowance mailed on Mar. 9, 2023, for U.S. Appl. No. 16/016,272, filed Jun. 22, 2018, 8 pages.
Notice of Allowance mailed on Dec. 13, 2023, for U.S. Appl. No. 17/375,586, filed Jul. 14, 2021, 12 pages.
Peng, C. et al. (Jun. 2016). "Chapter 15: Clinical radiotherapy technique," in *Clinical Diagnosis and Treatment of Oncological Diseases*, published by Jilin Science and Technology Press, first edition, first printing, p. 276 (with English translation).
Shiying, Y. (Jul. 2009). "Chapter 4: Design of radiotherapy plan," in *Guidelines for Standardized Diagnosis and Treatment of Tumors*,

(56) References Cited

OTHER PUBLICATIONS published by Huazhong University of Science and Technology Press, first edition, first printing, p. 106 (with English translation).
Xuening, Z. (Dec. 2010). "Chapter 2: Principles and Stereotactic Techniques of LEKSELL Gamma Knife," in *Gamma Knife Surgery for Intracranial Disease-Clinical Imaging*, published by Tianjin Science and Technology Press, first edition, first printing, pp. 29-30 (with English Translation).
Zhiliao, Z. et al. (Mar. 2002). "Progress in Physics of Tumor Radiotherapy," Beijing Medical University and China Union Medical University Joint Publishing House, first edition, first printing, pp. 163-164 (with English translation).
Extended European Search Report mailed on May 31, 2024, for EP Application No. 23 211 269.8, filed on Jun. 22, 2018, 5 pages.
Geets, X. et al. (Oct. 2007). "Adaptive biological image-guided IMRT with anatomic and functional imaging in pharyngo-laryngeal tumors: impact on target volume delineation and dose distribution using helical tomotherapy," Radiother. Oncol. 85(1):105-115.
Non-Final Office Action mailed on Jun. 24, 2024, for U.S. Appl. No. 18/295,448, filed Apr. 4, 2023, 8 pages.
Notice of Allowance mailed on May 9, 2024, for U.S. Appl. No. 17/571,273, filed Jan. 7, 2022, 15 pages.
Notice of Allowance mailed on Sep. 29, 2024, for U.S. Appl. No. 18/295,448, filed Apr. 4, 2023, 5 pages.
Supplemental Notice of Allowability mailed on Aug. 8, 2024, for U.S. Appl. No. 17/571,273, filed Jan. 7, 2022, 2 pages.

\* cited by examiner

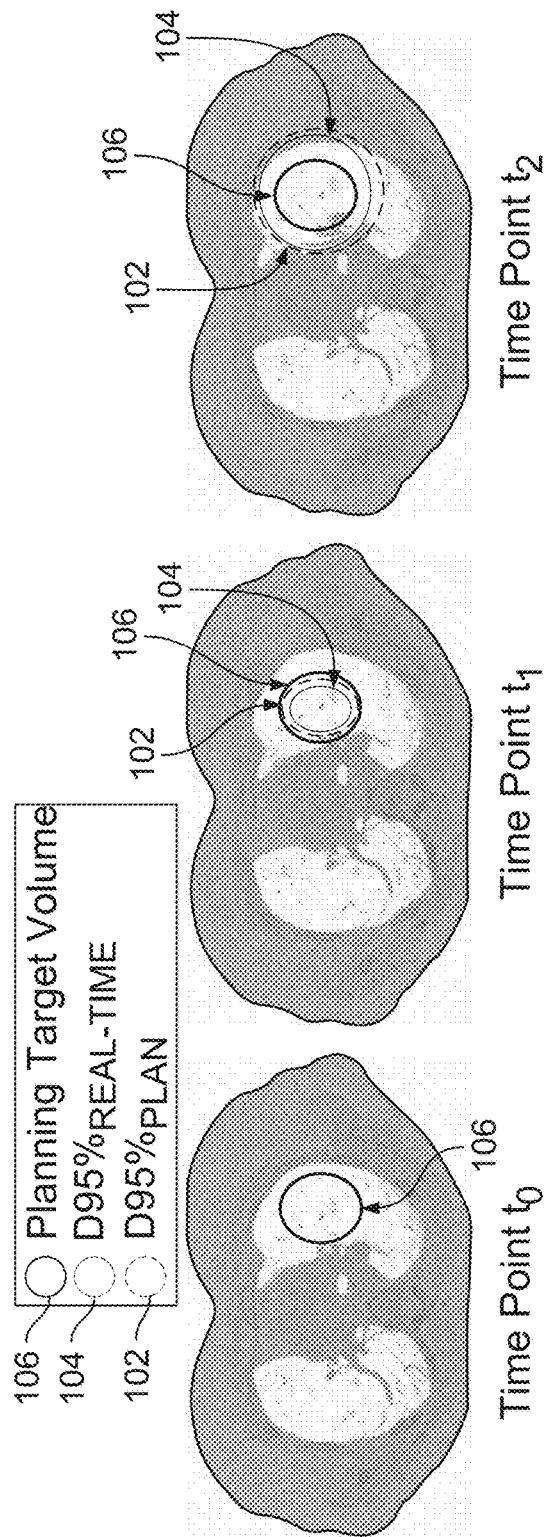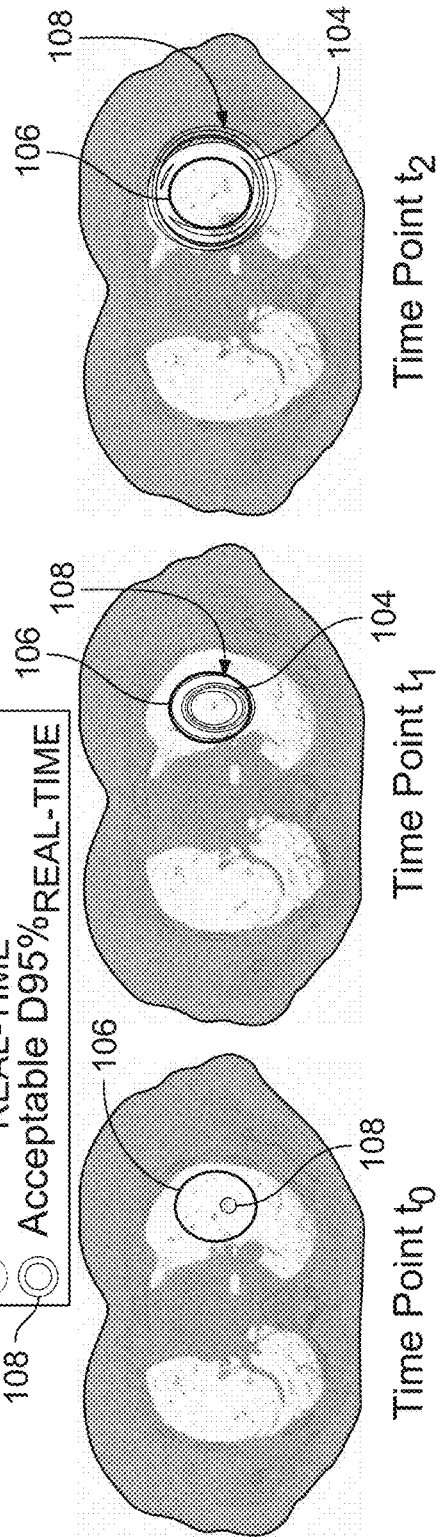

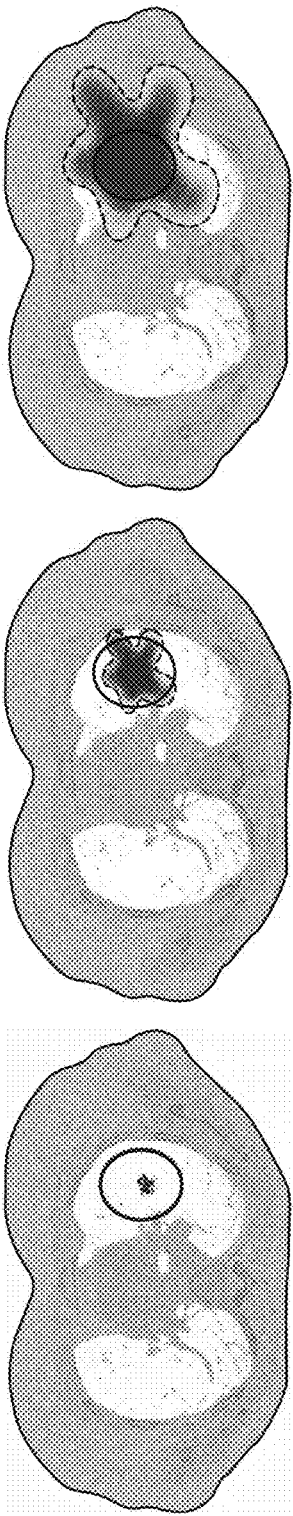
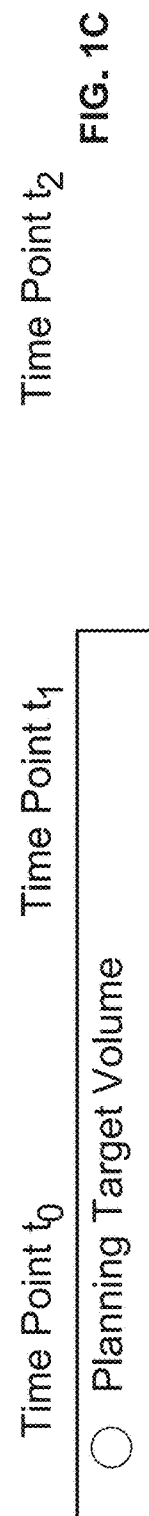
FIG. 1C
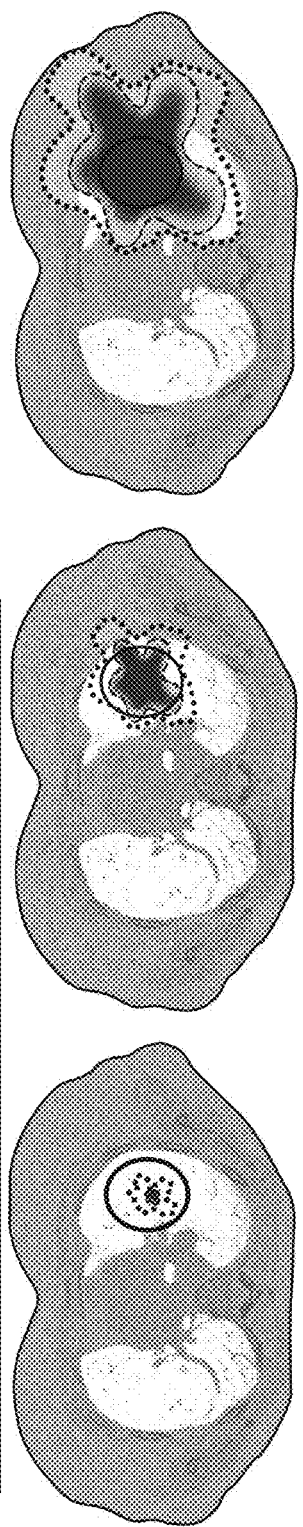
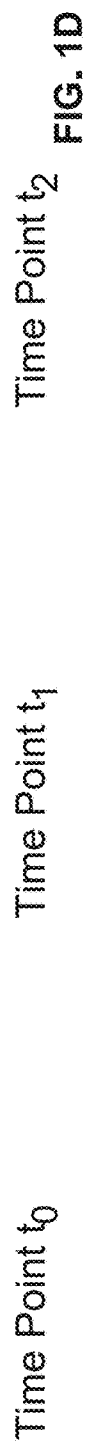
FIG. 1D

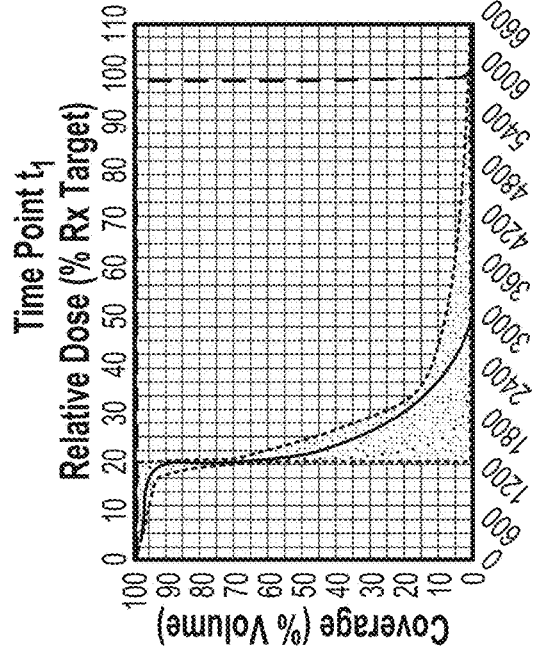
FIG. 2D
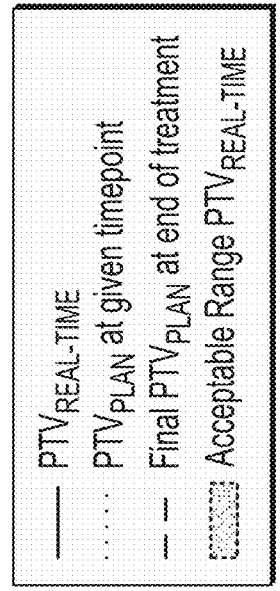
FIG. 2F
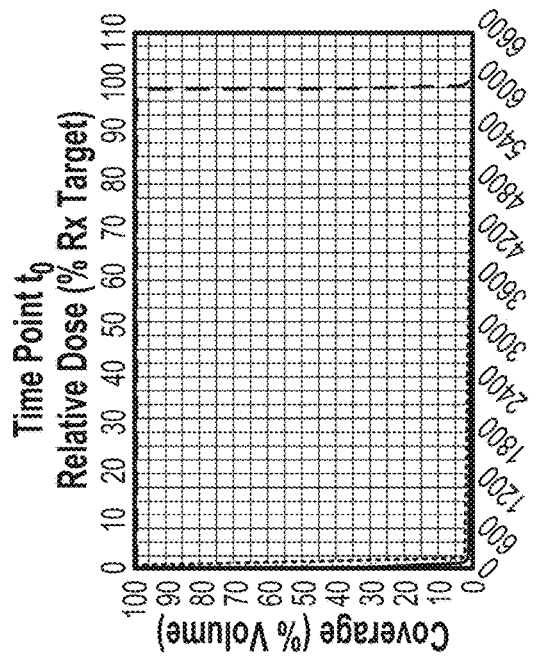
FIG. 2E
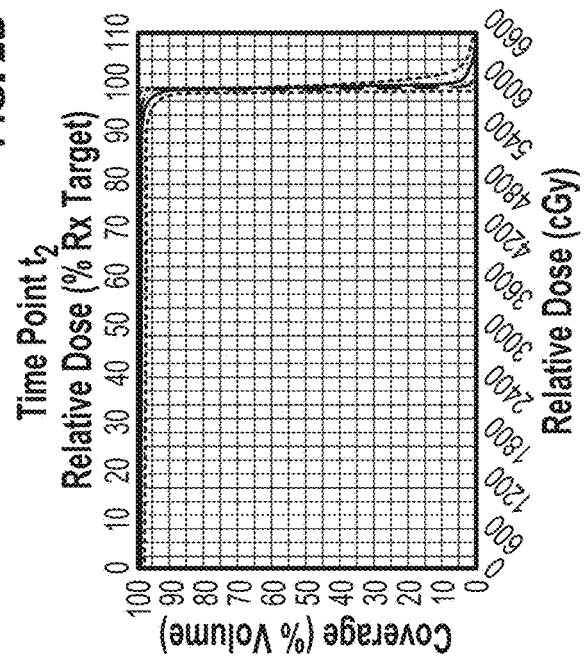

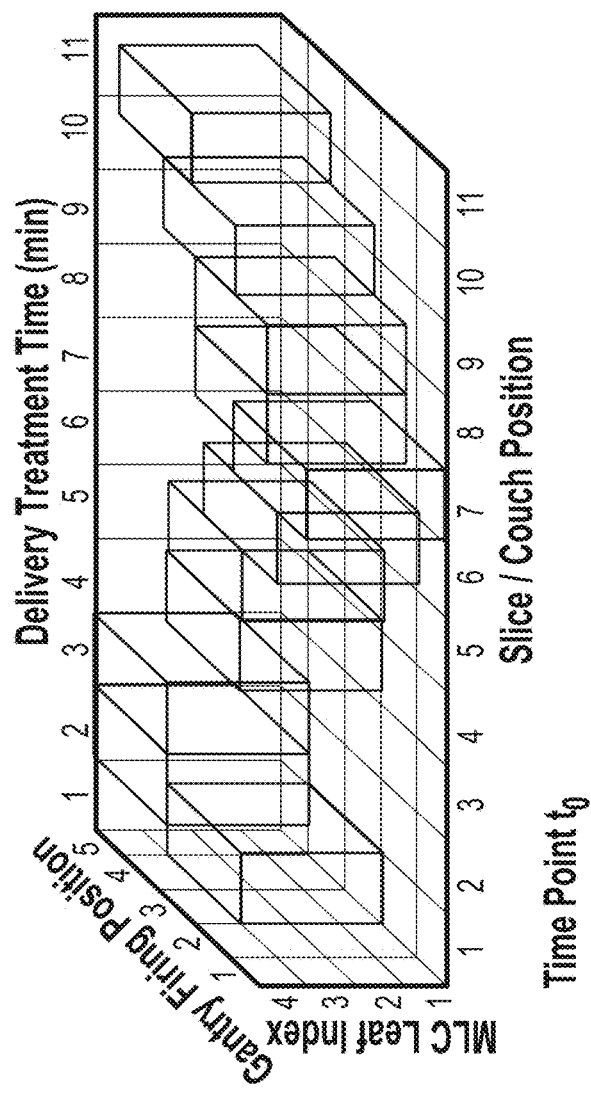
FIG. 4A
Time Point $t_0$
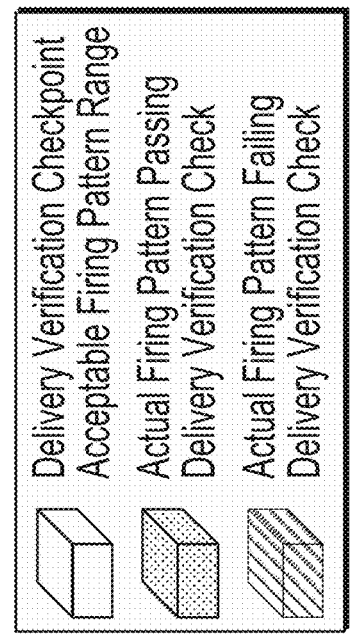
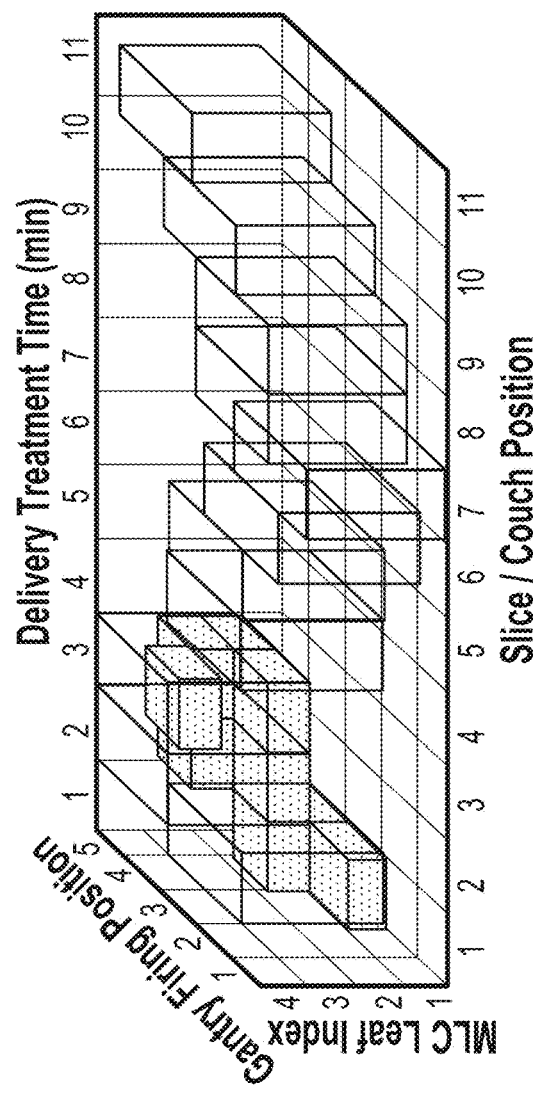
FIG. 4B

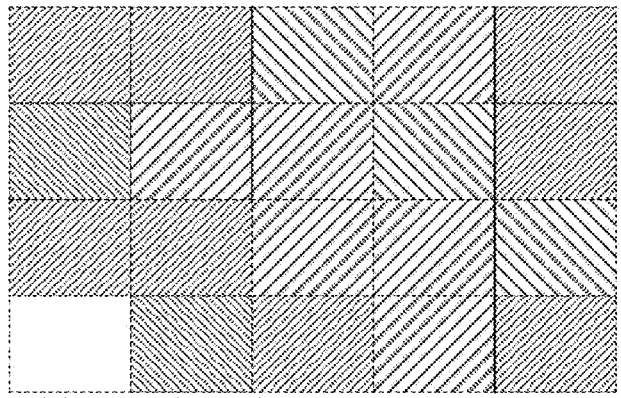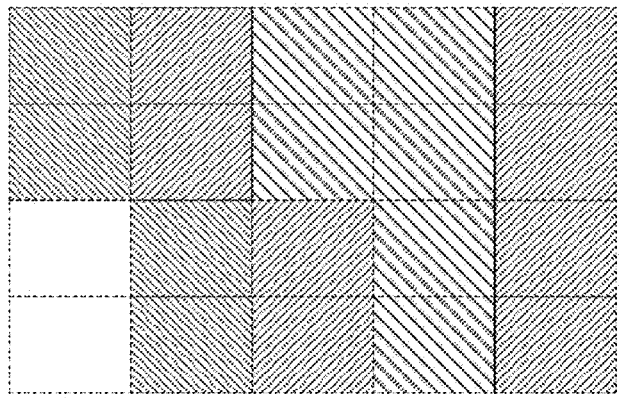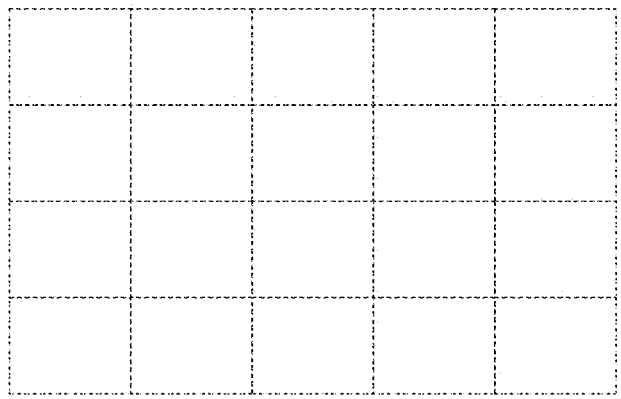
FIG. 5

Time Point $t_1$
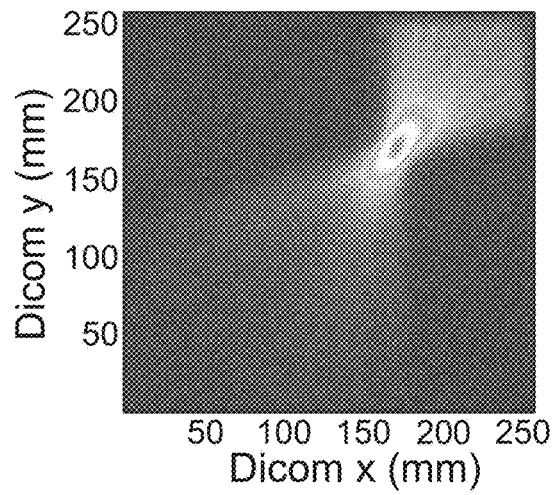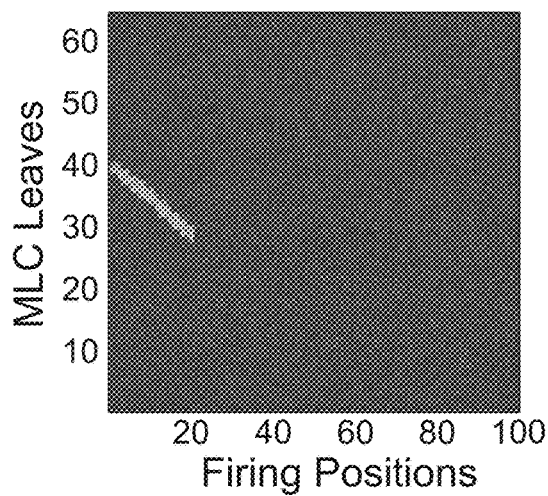
Time Point $t_2$
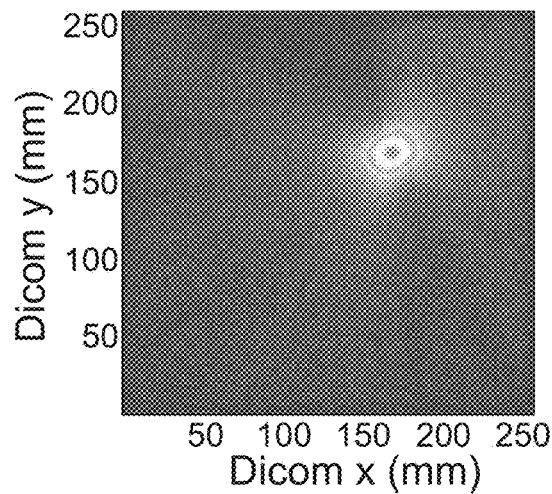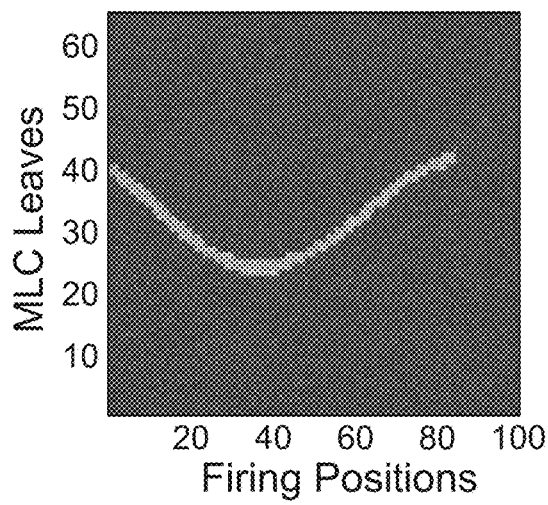
FIG. 6A

| Conceptual Volume | Objective | Parameters | Violations (Voxels) | Violations (%) | Tolerance (%) | Status |
|---|---|---|---|---|---|---|
| PTV_4500_7a [PTV_4500_7a] | Minimum Percent Volume at Dose | Dose (Gy): 45 Volume (%): 95 | 0 | 0.0% | 0.5 | Passed |
| PTV_4500_7a [PTV_4500_7a] | Minimum Percent Volume at Dose | Dose (Gy): 31.5 Volume (%): 99.5 | 0 | 0.0% | 0.5 | Passed |
| PTV_4500_7b [PTV_4500_7b] | Minimum Percent Volume at Dose | Dose (Gy): 45 Volume (%): 95 | 0 | 0.0% | 0.5 | Passed |
| PTV_4500_7b [PTV_4500_7b] | Minimum Percent Volume at Dose | Dose (Gy): 31.5 Volume (%): 99.5 | 0 | 0.0% | 0.5 | Passed |
| GTV_4500_7a_4 [GTV_4500_7a] | Prescription Dose | Dose (Gy): 45 | 0 | 0.0% | 0.5 | Passed |
| Lung, Left [Lung_L] | Maximum Absolute Volume at Dose | Dose (Gy): 12.3 Volume (cc): 130 | 0 | 0.0% | 0.5 | Passed |
| Lung, Left [Lung_L] | Maximum Percent Volume at Dose | Dose (Gy): 20 Volume (%): 37 | 0 | 0.0% | 0.5 | Passed |
| Lung, Right [Lung_R] | Maximum Percent Volume at Dose | Dose (Gy): 20 Volume (%): 37 | 0 | 0.0% | 0.5 | Passed |
| Spinal Cord [SpinalCord] | Maximum Absolute Volume at Dose | Dose (Gy): 22.5 Volume (cc): 0.03 | 0 | 0.0% | 0.5 | Passed |

FIG. 8A

| Conceptual Volume | Objective | Parameters | Violations (Voxels) | Violations (%) | Tolerance (%) | Status |
|---|---|---|---|---|---|---|
| Boosted PTV [PTV70] | Prescription Dose | Dose (Gy): 70 | 4704 | 4.7% | 0.5 | Failed |
| Boosted PTV [PTV70] | Minimum Percent Volume at Dose | Dose (Gy): 70 Volume (%): 95 | 0 | 0.0% | 0.5 | Passed |
| Boosted PTV [PTV70] | Maximum Percent Volume at Dose | Dose (Gy): 73.5 Volume (%): 0 | 20340 | 20.4% | 0.5 | Failed |
| Boosted PTV [PTV70] | Maximum Absolute Volume at Dose | Dose (Gy): 77 Volume (cc): 0.03 | 1997 | 2.0% | 0.5 | Failed |
| Non-Boosted PTV [PTV63] | Prescription Dose | Dose (Gy): 63 | 1104 | 0.5% | 0.5 | Needs Review |
| Non-Boosted PTV [PTV63] | Minimum Percent Volume at Dose | Dose (Gy): 63 Volume (%): 95 | 0 | 0.0% | 0.5 | Passed |
| Subclinical PTV [PTV56] | Prescription Dose | Dose (Gy): 56 | 12317 | 2.3% | 0.5 | Failed |
| Subclinical PTV [PTV56] | Minimum Percent Volume at Dose | Dose (Gy): 56 Volume (%): 95 | 0 | 0.0% | 0.5 | Passed |
| CTV [CTV56] | Minimum Percent Volume at Dose | Dose (Gy): 70 Volume (%): 99 | 16144 | 4.7% | 0.5 | Failed |
| Spinal Cord [SPINAL_CORD] | Maximum Absolute Volume at Dose | Dose (Gy): 48 Volume (cc): 0.03 | 0 | 0.0% | 0.5 | Passed |

FIG. 8B

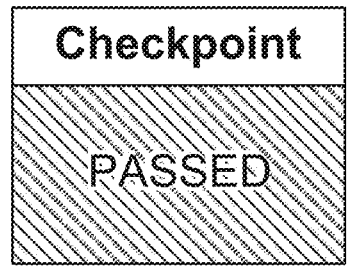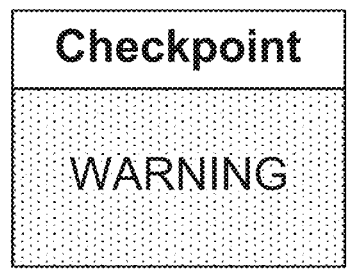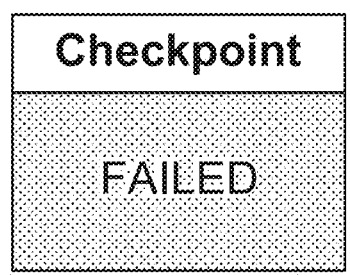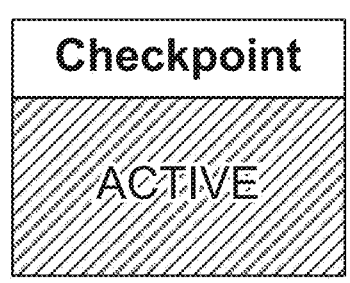
FIG. 9

GRAPHICAL REPRESENTATION OF RADIATION THERAPY

CROSS-REFERENCE TO RELATED APPLICATIONS

This application is a continuation of U.S. patent application Ser. No. 16/582,308, filed Sep. 25, 2019, which is a continuation of U.S. patent application Ser. No. 16/046,746, filed Jul. 26, 2018, now issued U.S. Pat. No. 10,456,600, which claims priority to U.S. Provisional Patent Application No. 62/537,422, filed Jul. 26, 2017, each of which is hereby incorporated by reference in its entirety.

TECHNICAL FIELD

This disclosure relates to radiotherapy systems and methods for generating graphical representations of the progress of radiation delivery during a radiation delivery session (e.g., a treatment session or treatment plan evaluation session). The graphical representations may provide an indication as to whether the radiotherapy system is generating radiation fluence and/or delivering radiation dose according to a treatment plan.

BACKGROUND

During a radiation treatment session, a patient is placed in a radiotherapy system and exposed to therapeutic doses of radiation that target tumor regions while avoiding radiation-sensitive structures (e.g., organs at risk or OARs). The therapeutic radiation source, beam-shaping components (e.g., jaws, multi-leaf collimator), as well as the gantry and motion system operate in concert in accordance with a radiotherapy treatment plan with the goal of irradiating one or more tumor regions with a prescribed dose of radiation. An operator (e.g., a clinician, medical physicist, radiation therapy technologist) may be present during the treatment session to monitor the radiotherapy system and to, for example, pause or terminate the treatment session if any machine fault is detected and/or if the patient can no longer tolerate the therapy. Some radiotherapy systems may generate log files containing data about the operation of the various components and/or hardware of the radiotherapy system (e.g., location of the therapeutic radiation source, number of emitted pulses, movement and/or position of the beam-shaping components, etc.) over time. By reviewing the log files, the operator may confirm that the hardware of the radiotherapy system is operating as specified by the radiotherapy treatment plan and that the prescribed radiation dose has been delivered. However, reviewing system log files may be cumbersome and may not provide an accurate indication of whether radiation delivery is proceeding according to the treatment plan. Accordingly, improved methods of monitoring radiation delivery may be desirable.

SUMMARY

Described herein are methods for monitoring the radiation delivery during a radiotherapy treatment session and generating a graphical representation of radiation delivery that may be provided to an operator (e.g., a clinician, a medical physicist, a radiation therapy technologist). The progress of radiation delivery during a treatment session relative to planned radiation delivery (i.e., as specified by a radiotherapy treatment plan) may be displayed to the operator, who may use this information to decide whether to continue radiation delivery, adjust certain parameters to help radiation delivery conform more closely to the planned radiation fluence and/or dose profile, and/or to pause or cease radiation delivery. The graphics may be updated in real-time, as radiation data and/or radiotherapy system hardware data is collected by the radiotherapy system controller, and in some variations, may be updated every 15 minutes or less (e.g., about 12 minutes or less, about 10 minutes or less, about 8 minutes or less, about 5 minutes or less, about 2 minutes or less). The graphics may alternatively or additionally be updated at pre-determined time points or control points during the session. Control points may comprise a list of radiotherapy system component configurations pertinent to the delivery of therapeutic radiation. In some variations, control points may comprise a list of firing positions or arrangements of the therapeutic radiation source (e.g., as defined by radiation source gantry angle, patient platform position, configuration(s) of one or more beam-shaping components such as one or more multi-leaf collimators and/or jaws) relative to the patient. Control points may also comprise a list of different gantry motions and/or positions of the therapeutic radiation source, and/or different multi-leaf collimator leaf configurations, and/or patient platform positions, and/or therapeutic radiation source dose rates, and the like. A variety of graphical representations ("graphics") may be used to indicate the status of radiation delivery relative to the planned radiation delivery, and may provide a radiation delivery profile over time. Methods may optionally comprise calculating a range of acceptable metric values, generating graphics that represent the range of acceptable metrics values, and comparing the actual values of those metrics (calculated based on real-time acquired data) with the range of acceptable metrics values.

Methods described herein may also comprise calculating expected or planned radiation delivery metrics at pre-determined or pre-selected time points and/or checkpoints based on the treatment plan before the treatment session, calculating the actual or current radiation delivery metrics at those pre-determined time points during the treatment or quality assurance (QA) session, and generating one or more graphics that depict the progress of actual or current radiation delivery as compared to expected or planned delivery at those time points or checkpoints. These graphics may help provide an indication to the operator as to the accuracy and/or precision of radiation delivery, which may aid the operator in deciding whether radiation delivery should continue or be paused/stopped. The methods described herein may optionally be used during a treatment plan verification or QA session, and provide a graphical representation of radiation delivery to a phantom during the session as compared to the planned radiation delivery.

One variation of a radiotherapy system for monitoring radiation delivery and generating graphical representations of the radiation delivery may comprise a rotatable gantry, a gantry position sensor coupled to the rotatable gantry, a therapeutic radiation source mounted on the rotatable gantry and movable to a plurality of gantry firing positions by rotating the gantry, a radiation detector disposed in a radiation beam path of the therapeutic radiation source, a beam-shaping component disposed in the radiation beam path of the therapeutic radiation source, the beam-shaping component configured to have a radiation-transmitting aperture with a size and shape, a beam-shaping component sensor configured to detect the size and shape of the radiation-transmitting aperture, and a display in communication with a controller. The controller may comprise a machine-readable memory medium storing a value of a planned radiation delivery metric over time, and a processor. The processor may be configured to calculate a real-time value of the radiation delivery metric at multiple time points during a radiation delivery session based on data acquired from the gantry position sensor and/or radiation detector and/or beam-shaping component sensor during the radiation delivery session, generate a graphical representation depicting the planned radiation delivery metric value and the real-time radiation delivery metric value over the multiple time points, and output the graphical representation to the display. The machine-readable memory medium may be configured to store a pre-selected range of values of the planned radiation delivery metric, and the processor may be configured to generate a graphical representation of the pre-selected range of planned radiation delivery metric. The processor may be configured to calculate the real-time value of the radiation delivery metric, generate the graphical representation, and output the graphical representation to the display about every 15 minutes or less, e.g., about every 10 minutes or less, about every 5 minutes or less, about every minute or less, about every 10 seconds or less, etc. The controller may be configured to compare the planned radiation delivery metric with the real-time value of the radiation delivery metric, and to generate a graphical representation depicting whether or not the real-time value is within the pre-selected range of values of the planned radiation delivery metric. The controller may be configured to generate a command signal for stopping radiation delivery if the real-time radiation delivery metric is out of the pre-selected range of the planned radiation delivery metric. Alternatively or additionally, the controller may be configured to generate and output warnings to the display when the real-time radiation delivery metric is near the boundaries of the pre-selected range of the planned radiation delivery metric. In some variations, the radiation delivery metric may be a dose-volume metric generated using data acquired during the radiation delivery session by the gantry position sensor, the radiation detector, the beam-shaping component sensor, and/or an image of a patient or phantom. For example, the radiation delivery metric may comprise an isodose contour and the graphical representation may comprise isodose contour lines superimposed over the image of the patient or phantom. The image may contain structural images of the patient or phantom acquired during the radiation delivery session, e.g., the image may be a PET and/or CT scan of the patient or phantom acquired during the radiation delivery session. Alternatively or additionally, the image of the patient or phantom may contain structural images of the patient or phantom acquired before the radiation delivery session. The radiation delivery metric may comprise volumetric dose accumulation and the graphical representation comprises a dose-volume histogram. The dose-volume histogram may be updated at pre-determined time intervals within the radiation delivery session. The graphical representation may include a planned dose-volume histogram and one or more bounds delineating a preselected range of dose-volume histogram values. The radiation delivery metric may comprise a dose gradient build-up and the graphical representation may comprise the dose gradient superimposed over the image of the patient or phantom. In some variations, the planned radiation delivery metric over time may comprise a first sinogram that designates the size and shape of the radiation-transmitting aperture of the beam-shaping component for each gantry firing position according to a treatment plan, and the graphical representation may comprise the first sinogram and a second sinogram that represents the size and shape of the radiation-transmitting aperture for each gantry firing position using data acquired during the radiation delivery session from the beam-shaping component sensor and the gantry position sensor.

The beam-shaping component may comprise a dynamic multi-leaf collimator (MLC) having a plurality of leaves and the beam-shaping component sensor may comprise a plurality of leaf position and/or motion sensors coupled to the plurality of leaves. The first sinogram may designate positions of the plurality of leaves for each gantry firing position based on a segmented treatment plan fluence map, and the second sinogram may represent the positions of the plurality of leaves for each gantry firing position using data from the plurality of leaf position and/or motion sensors and the gantry position sensor. The system may optionally comprise a patient platform movable through a plurality of platform positions within a bore of the gantry and along an axis of rotation of the gantry, and the graphical representation may optionally comprise a 3-D sinogram that is a combination of the first sinogram and the second sinogram for each of the plurality of platform positions. In some variations, the graphical representation may comprise a pseudo-color firing map, where an intensity of each cell in the pseudo-color firing map may represent a frequency or intensity of radiation delivery for each MLC leaf at each gantry firing position calculated using data from the gantry position sensor, radiation detector, and leaf position and/or motion sensors acquired during the radiation delivery session. The real-time value of the radiation delivery metric may be a radiation dose distribution generated using data from the gantry position sensor, radiation detector, and leaf position and/or motion sensors acquired during the radiation delivery session, and the graphical representation may optionally comprise a simulated view of the radiation dose distribution in a gantry bore along an axis of rotation of the gantry. For example, the simulated view may visualize the radiation beam paths of the radiation source during the radiation delivery session, e.g., the simulated view may visualize a dose accumulation within the gantry bore.

The radiation detector may comprise an ionization chamber. The rotatable gantry may comprise a rotatable ring having a rotor element and a stationary frame having a stator element, and the gantry position sensor may comprise an encoder configured to detect the relative positions of the rotor element and the stator element. In some variations, the gantry position sensor may comprise an inclinometer and/or an accelerometer.

BRIEF DESCRIPTION OF THE DRAWINGS

FIG. 1A depicts one example of a graphical representation comprising isodose contours.

FIG. 1B depicts one example of a graphical representation comprising isodose contours and a pre-selected range of acceptable isodose contour values.

FIG. 1C depicts one example of a graphical representation comprising dose gradients.

FIG. 1D depicts one example of a graphical representation comprising dose gradients and a pre-selected range of acceptable dose gradient boundaries.

FIGS. 2D-2F depict one example of a graphical representation comprising bounded DVH curves.

FIG. 4A depicts one example of a graphical representation comprising a 3-D bitmask or sinogram at a first time point.

FIG. 4B depicts one example of a graphical representation comprising a 3-D bitmask or sinogram at a second time point.

FIG. 5 depicts one example of a graphical representation comprising a pseudocolor representation of firing accumulation over time.

FIG. 6A depicts one example of a graphical representation comprising a dose accumulation displayed with a virtual bore.

FIG. 8A depicts one example of a graphical representation comprising a table summarizing dosimetric objectives and plan quality indices and their status during a delivery session.

FIG. 8B depicts one example of a graphical representation comprising a table summarizing dosimetric objectives and plan quality indices and their status during a delivery session.

FIG. 9 depicts one example of a graphical representation comprising possible status or states of delivery metric values or criteria at a check point.

DETAILED DESCRIPTION

Figure 2A:
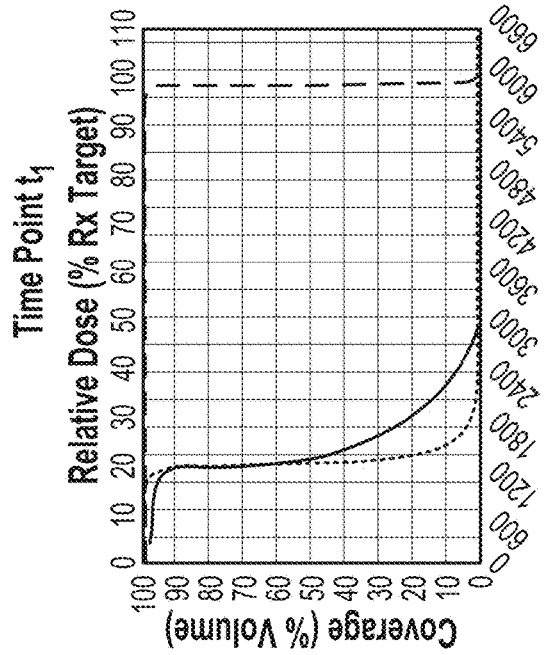
FIGS. 2A-2C depict one example of a graphical representation comprising DVH curves.

Described herein are methods for monitoring the radiation delivery during a radiotherapy treatment session and generating a graphical representation of radiation delivery that may be provided to an operator (e.g., a clinician, a medical physicist, a radiation therapy technologist). A graphical representation ("graphic") of radiation delivery may be any visual indicator, including but not limited to, images, graphs, diagrams, symbols, maps, drawings, plots, tables, alphabetic characters, numeric characters, and/or alphanumeric characters, that represents the value(s) of a radiation delivery metric at one or more time points during a delivery session (e.g., QA session, treatment session). The progress of radiation delivery during a treatment session relative to planned radiation delivery (i.e., as specified by a radiotherapy treatment plan) may be displayed to the operator, who may use this information to decide whether to continue radiation delivery, adjust certain parameters to help radiation delivery conform more closely to the planned fluence and/or dose profile, and/or to pause or cease radiation delivery. In some variations, graphical representations of radiation delivery may include visual indicators of the planned value of the radiation delivery metric at a particular time point during the delivery session and the actual value of the delivery metric (calculated based on real-time acquired data) in a way that allows the real-time value of the delivery metric to be visually compared to the planned value of the delivery metric. In addition to patient treatment sessions, the methods described herein may be used during a treatment plan verification or quality assurance (QA) session, and provide a graphical representation of radiation delivery to a phantom or another radiation-measurement device during the session as compared to the planned radiation delivery. The graphics may be updated in real-time, as radiation data is collected by the radiotherapy system, and in some variations, may be updated every 15 minutes or less (e.g., about 12 minutes or less, about 10 minutes or less, about 8 minutes or less, about 5 minutes or less, about 2 minutes or less). The graphics may alternatively or additionally be updated at pre-determined time points or control points during the session. A variety of graphics may be used to indicate the status of radiation delivery relative to the planned radiation delivery, and may provide a radiation delivery profile over time. For example, graphics may include one or more of dose-volume plots, beam-firing patterns, 4-D dose images, and/or dosimetric objective and plan quality comparisons. The graphic(s) displayed to an operator during radiation delivery may be selected by the operator at the time of treatment and/or may be pre-selected based on clinical guidelines or requirements. For example, an operator may select one graphic for display during radiation delivery, or multiple graphics for display. While the example graphics described herein are depicted in black and white or grayscale, it should be understood that these and other graphics may be colorized (e.g., 8-bit or 256-bit color levels). Methods may optionally comprise calculating a range of acceptable metric values, generating graphics that represent the range of acceptable metric values, and comparing the actual values of those metrics (calculated based on real-time acquired data) with the range of acceptable metric values.

Methods described herein may also comprise calculating expected or planned radiation delivery metrics based on the treatment plan at pre-determined or pre-selected time points before the treatment session, calculating the actual or current radiation delivery metrics at those pre-determined time points during the treatment or QA session, and generating one or more graphics that depict the progress of actual or current radiation delivery as compared to expected or planned delivery. These graphics may help provide an indication to the operator as to the accuracy, and/or precision, and/or safety of radiation delivery, which may aid the operator in deciding whether radiation delivery should continue or be paused/stopped.

In some variations, methods for monitoring the progress of radiation delivery may comprise calculating the expected values of radiation delivery metrics and/or an expected radiation delivery profile before a treatment session. For example, a radiation delivery metric that reflects the cumulative delivered dose to one or more target regions may be calculated based on the treatment plan as a function of time, where the value of the metric increases progressively until the full prescribed dose is delivered at the end of the treatment session. The value of a radiation delivery metric may be calculated at pre-determined or specified time intervals or control points, for example, at every tenth of the duration of the treatment session (e.g., 10%, 20%, 30%, . . . 70%, 80%, 90%, 100% of the treatment session time), or every n time interval (e.g., for n=2 seconds, 4 seconds, 5 seconds, 6 seconds, 10 seconds, 30 seconds, 60 seconds, 2 minutes, 4 minutes, 5 minutes, 10 minutes, 12 minutes, 15 minutes, or any other selected time interval). The expected values of radiation delivery metrics may be calculated during the treatment planning session and/or any time before the treatment session (i.e., before the therapeutic radiation beam is activated for treatment). In some variations, a method may comprise calculating a range of acceptable radiation delivery metric values within which treatment can proceed. The range of acceptable radiation delivery metric values may be represented by a "band" defined by a lower bound and an upper bound, where metric values within the band (i.e., between the upper and lower bounds) may be considered acceptable radiation delivery progress. Optionally, the range of radiation delivery metric values may be reviewed and approved by a clinician prior to the treatment session.

While the various graphics described herein are depicted as standalone graphical representations of radiation delivery, it should be understood that in some variations, multiple of these graphics may be selected for simultaneous display on a radiotherapy system display, and/or may be customized by an operator. Graphics selections and settings may be saved in a memory of the radiotherapy system controller, and associated with a particular operator so that whenever that particular operator logs in to the radiotherapy system, the graphical user interface reflects their previously-selected settings and preferences.

Systems

Figure 10A:
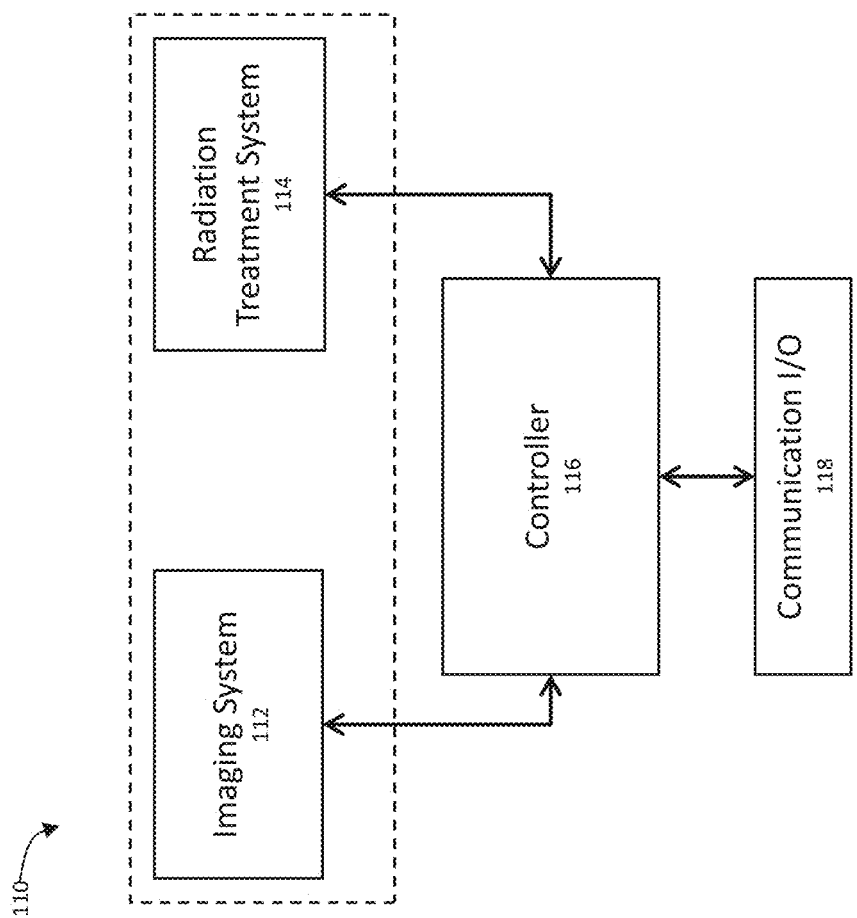
FIG. 10A depicts one variation of a radiotherapy system.

The radiation delivery metrics and graphical representations described herein may be used with any radiotherapy system to monitor and track the progress of a radiation delivery session (e.g., a treatment session and/or a QA session). For example, any of the radiation delivery metrics and the graphical representations described herein may be used with a radiotherapy system comprising a rotatable gantry (e.g., a circular gantry, armed gantry such as a C-arm gantry, etc.), a therapeutic radiation source (e.g., a linear accelerator or linac) mounted on the gantry, one or more beam-shaping components or structures (e.g., a collimator, such as a dynamic MLC, binary dynamic MLC, and/or one or more jaws) disposed in the radiation path of the therapeutic radiation source, and a radiation detector mounted on the gantry in the radiation beam path (e.g., opposite, or directly across from, the therapeutic radiation source). In some variations, a radiotherapy system may comprise one or more PET detectors, and/or X-ray detectors (e.g., kV X-ray detectors), and/or MM detectors, and/or optical cameras or imagers. FIG. 10A schematically depicts one variation of a radiotherapy system. Radiotherapy system 110 may comprise an imaging system 112, a radiation treatment system 114, a controller 116 in communication with the imaging system and the radiation treatment system, and a communication interface 118. The imaging system 112 and the radiation treatment system 114 may be arranged such that a patient may be readily positioned in the radiation treatment system immediately after patient image data has been acquired by the imaging system. For example, the imaging system 112 and the radiation treatment system 114 may be located in the same facility or building, and/or the same room or bunker, and/or may be mounted on the same chassis or gantry. The radiation treatment system 114 may comprise a therapeutic radiation source (e.g., a linac), one or more beam-shaping components (e.g., jaws, MLC) located within the beam path of the radiation source, and a radiation detector (e.g., MV detector) located within the beam path of the radiation source. The imaging system 112 may be configured to acquire imaging data using any one or more imaging modalities, including functional and/or anatomical imaging modalities, as long as the imaging system is capable of acquiring data during a treatment session (i.e., in real-time). The imaging system 112 may comprise one or more PET detectors, and/or X-ray detectors (e.g., kV or MV detectors), and/or MM sensors, ultrasound detectors, etc. Imaging data from the imaging system 112 may provide biological activity and/or physiological and/or anatomical data relating to the patient's body and/or one or more target regions or volumes-of-interest. Some imaging systems may acquire data relating to the uptake of various types of tracers in the patient's body. For example, a patient may be injected with a tracer (e.g., PET tracer, X-ray contrast agent, and the like), and the imaging system may acquire data regarding the accumulation of the tracer (qualitatively and/or quantitatively). The tracer accumulation location, size and shape of the tracer accumulation volumes, as well as tracer kinetics may provide an indication of various biological activity levels and/or physiological phenomena in the patient. While some imaging systems may be configured to acquire imaging data at any time point (and/or control point and/or checkpoint, as may be desired), regardless of the activation state of the radiation treatment system (e.g., regardless of whether the therapeutic radiation source is activated), other imaging systems may be configured to acquire imaging data when the therapeutic radiation source of the radiation treatment system is not activated (e.g., not firing a radiation beam). For example, an imaging system comprising one or more X-ray detectors may acquire imaging data between therapeutic radiation beam pulses, and/or when the therapeutic radiation source is not activated (due to the effects of X-ray scatter from a high-energy radiation source). An imaging system comprising one or more PET detectors may acquire PET data between therapeutic radiation beam pulses, and/or at the start of a treatment session before the first therapeutic radiation pulse and/or at the end of the treatment session after the last therapeutic radiation pulse. In contrast, an imaging system that comprises one or more MM sensors may acquire imaging data regardless of whether the therapeutic radiation source is activated and/or applying a radiation beam pulse. The radiation treatment system may comprise a therapeutic radiation source (e.g., an MV X-ray radiation source such as a linac, a radioactive isotope source such as a Cobalt-60 source, or a particle beam source such as a cyclotron), one or more beam-shaping components that may be configured to direct or limit the therapeutic radiation beam, and a motion system configured to rapidly move the therapeutic radiation source and the beam-shaping components to various firing positions around the patient area. Other examples of therapeutic radiation sources may include, but are not limited to, high energy photons, radiation or particles produced by a radioactive isotope (e.g. iridium or cobalt-60), high energy electrons, a proton beam, a neutron beam and a heavy ion beam. In one variation, a radiation treatment system may comprise a MV X-ray radiation source and a dynamic multi-leaf collimator disposed in the beam path of the radiation source, both mounted on a motion system comprising a movable gantry. The gantry may be a rotatable gantry, such as a circular gantry or a L-arm or C-arm gantry, and/or an articulated robotic arm movable and/or rotatable about the patient area. The gantry may optionally be a continuously rotating gantry. The motion system may be configured to move the radiation source and beam-shaping components from one firing position to another firing position in less than about 10 seconds, for example, less than about 5 seconds, less than about 3 seconds, less than about 2 seconds, less than about 1 second, less than about 0.5 second, less than about 0.25 second, etc.

The dynamic multi-leaf collimator may comprise a plurality of leaves, each leaf attached to a leaf actuation mechanism that moves the leaf to a location designated by the controller. The dynamic multi-leaf collimator may be a binary multi-leaf collimator or a 2-D multi-leaf collimator. Other beam-shaping components or collimators may also be used, for example, radial collimators that generate circular fields. The leaf actuation mechanism may be configured to rapidly move the leaf from one position to another position before the radiation source fires the next beam pulse. For example, in a binary multi-leaf collimator, the leaf actuation mechanism may be configured to transition a leaf from a closed position to an open position (and vice versa) in less than about 5 seconds, e.g., less than about 3 seconds, less than about 2 seconds, less than about 1 second, less than about 0.5 second, less than about 0.75 second, less than about 0.5 second, less than about 0.3 second, less than about 0.25 second, less than about 0.2 second, less than about 0.1 second, etc. The combination of a rapid-movement motion system and rapid-transitioning dynamic multi-leaf collimator may help reduce the latency between the acquisition of imaging data and the application of a radiation beam pulse based on biological activity data extracted from the imaging data. The position of the leaves at a particular firing location (e.g., location around a patient area where the therapeutic radiation source may be positioned when firing radiation beams) may be determined based on a treatment plan.

In some variations, the processor of the controller may generate a set of multi-leaf collimator commands that drive the movement and location of each leaf at each firing location so that the radiation beam has an irradiation shape that adheres to a treatment plan fluence map. A treatment plan fluence map may designate the amount of radiation (i.e., radiation fluence or radiation energy fluence) that is emitted to each portion of a patient's body, and in particular, to the one or more target regions or volumes-of-interest and/or OARs. A fluence map may comprise a set of beamlet intensities and firing positions (e.g., firing angles) that may be used by a radiotherapy system to position a therapeutic radiation source and to control the intensity and shape of the generated radiation beam such that a selected/prescribed dose of radiation is applied to target region(s) or volume(s)-of-interest while limiting the amount of radiation applied to one or more organs-at-risk or OARs (e.g., irradiation-avoidance volumes). The method by which a fluence map is converted into a set of radiotherapy system component comments or instructions may be referred to as segmentation of a treatment plan fluence map. A segmented fluence map may comprise commands or instructions for the radiation emission of the therapeutic radiation source (e.g., radiation firing intensity levels, magnitude of the radiation applied, and/or duty cycle and/or frequency and/or width of radiation pulses, etc.) at each gantry firing position about the patient (e.g., gantry firing angles), as well as the MLC leaf configuration corresponding to each of the firing positions, and/or patient platform position relative to the therapeutic radiation beam plane. The controller 116 may be in communication with the imaging system 112 and the radiation treatment system 114 such that acquired imaging data and/or any system sensor data may be combined to generate radiation delivery metric values and/or graphics that represent the progress of radiation delivery. The controller 116 may comprise one or more processors (e.g., a central processing unit) and one or more memories. A controller memory may store data relating to one or more treatment plans, treatment plan parameters (e.g., fluence map, plan quality indices, dose-volume histograms, etc.), previously-collected imaging and/or sensor data (e.g., from a diagnostic imaging session), real-time imaging and/or sensor data (e.g., acquired on the day of a treatment session, at the time of treatment), radiation treatment system commands and instructions, user-implemented programs, and the like. The controller 116 may receive imaging data and imaging component feedback (e.g., status of image detectors or sensors, calibration data, etc.) from the imaging system 112, and may also transmit imaging commands (e.g., activation of any X-ray source, and/or activation of the image detectors or sensors, adjustments to detector gain and/or sensitivity levels, positioning of the imaging system relative to the patient and/or radiation treatment system, etc.) to the imaging system. The controller 116 may receive data from the various components of the radiation treatment system and may transmit commands to the radiation treatment system. For example, the radiation treatment system may comprise a motion system (e.g., gantry), a therapeutic radiation source (e.g., linac) and beam-shaping component (e.g., dynamic MLC) mounted on the motion system, and a radiation detector (e.g., MV detector) mounted on the motion system. The controller 116 may receive positional and/or speed data from the motion system, positional and/or radiation beam generation data from the radiation source, leaf-configuration data from the beam-shaping component, and/or more generally, operating status, calibration data, error indicators, and the like. The controller 116 may transmit MLC commands, gantry rotation/motion commands, linac pulse instructions, etc., where these commands and instructions may be generated based on a combination of treatment plans, previously-acquired images, real-time acquired imaging and/or sensor data, biological activity and/or physiological data of the patient, and/or the state of the radiotherapy system. The controller 116 may be in communication with a display via communication interface 108, which may project any of the graphical representations (e.g., graphical user interface(s)) described herein to the operator. The graphical user interface may also provide a menu of commands for operator selection, as well as a programming interface so that the operator may enter a predetermined set of machine instructions and parameters. For example, the display may present one or more visual indicators that represent a graphical representation of the expected value of radiation delivery metrics and/or expected radiation delivery profile(s) as compared to the real values of those metrics and/or graphics based on acquired imaging and/or sensor data.

Figure 10B:
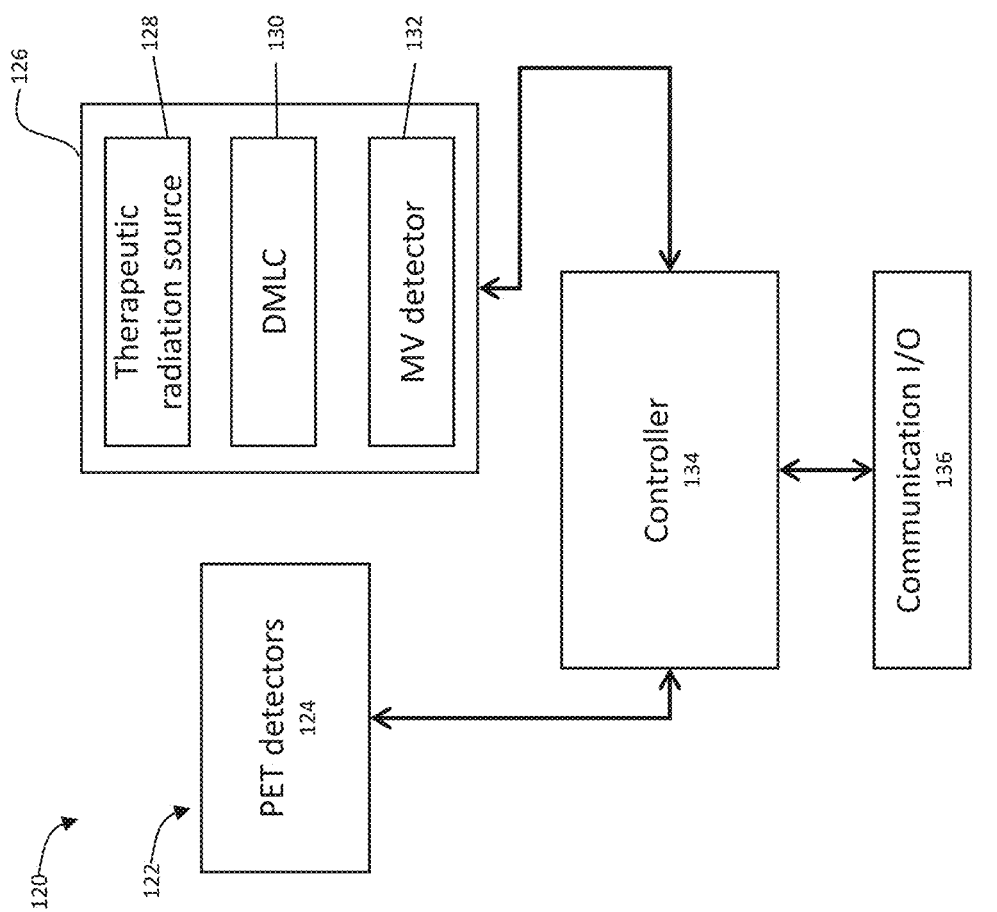
FIG. 10B depicts one variation of a radiotherapy system.

FIG. 10B depicts one variation of a radiotherapy system. Radiotherapy system 120 may comprise an imaging system 122 comprising one or more PET detectors 124, a radiation treatment system 126 comprising a therapeutic radiation source 128 (e.g., a MV X-ray source such as a linac), a dynamic MLC or DMLC 130, and an MV detector 132. The system 120 may also comprise a controller 134 in communication with the imaging system and the radiation treatment system 126 and a communication interface 136. The radiation emission assembly may be mounted on a movable gantry, such a rotatable gantry. In some variations, the rotatable gantry may be a continuously-rotatable circular gantry. Optionally, the imaging system 122 may also be mounted on the movable gantry. PET data (e.g., one or more individual positron annihilation emission paths) acquired by the one or more PET detectors 124 may be transmitted to the controller 134, which may be stored in controller memory and/or processed according to any of the methods described herein. The controller 134 may calculate and/or extract biological activity and/or physiological data from the PET data, which may optionally be presented to the clinician. The radiation treatment system 126 may move the therapeutic radiation source 128, change the DMLC leaf configuration, and acquire data from the MV detector in accordance with commands from the controller 134. In some variations, the gantry may be configured to rotate at about 40 RPM or more, e.g., about 60 RPM, about 70 RPM. The DMLC 130 may comprise leaf actuation mechanisms that change leaf positions within the time interval where the gantry is moving the radiation emission assembly from one firing position to another. For example, the DMLC 130 may comprise a leaf actuation mechanism that is configured to move a leaf from a fully closed position to a fully open position in less than about 10 ms. In some variations, a circular gantry that rotates with a frequency f having n firing positions may have a DMLC transition time that is less than 0.7*(f/n) seconds. For example, a circular gantry that rotates with a frequency f of about 1 Hz, having n=100 firing positions, may have a DMLC transition time of about 7 ms. A DMLC may comprise a leaf actuation mechanism comprising a pneumatic cylinder and one or more springs, which may provide sufficient motive force to change leaf position in the time interval between firing positions. Additional details and examples of multi-leaf collimator leaf actuation mechanisms, as well as radiotherapy systems are provided in U.S. patent application Ser. No. 15/179,823, filed Jun. 10, 2016 and U.S. patent application Ser. No. 15/814,222, filed Nov. 15, 2017, which are hereby incorporated by reference in their entirety.

In addition to one or more PET detectors, and/or X-ray detectors (e.g., kV or MV detectors), and/or MRI sensors, ultrasound detectors, etc., a radiotherapy system may comprise a plurality of sensors associated with one or more of the above radiotherapy components above. The data acquired by those sensors may be used to calculate the fluence (i.e., radiation fluence and/or radiation energy fluence) emitted by the linac that is directed to the patient, and/or the dose delivered to the target region or volume-of-interest during a treatment session to monitor the progress of radiation delivery. The emitted fluence and/or delivered dose may be represented by the one or more graphics and/or other visual indicia (e.g., including tables, charts, metric values or scores, etc.) may be displayed to the operator on a monitor or screen. During a treatment session (and/or directly after a treatment session, i.e., when the therapeutic radiation source is turned off), the radiotherapy system controller may acquire data from a variety of sensors in the system and calculate the values of the radiation delivery metric(s) in real-time. The values of the radiation delivery metric(s) may be calculated and stored over treatment session time, for example, at pre-determined or specified time intervals, time points, or control points. The controller may acquire data from one or more radiation detectors (e.g., a radiation detector located within the beam path of the therapeutic radiation source, MV detector located opposite or across from a linac), MLC position and/or movement sensors, PET detectors located on the therapy ring (for biology-guided radiotherapy treatments), therapeutic radiation source (e.g., linac) sensing detectors (e.g., for detecting pulse frequency, energy, duty-cycle, pulse count, etc.), dose or ionization chamber, etc., gantry or motion system position sensor(s), and/or any optical cameras located on a radiotherapy system and/or within the treatment bunker. The acquired data may be used to calculate the real-time value of one or more radiation delivery metrics, and a graphical representation of the radiation delivery metrics in real-time may be displayed to the operator. In some variations, the real-time radiation delivery metrics may be superimposed over the expected values of the radiation delivery metrics calculated before the treatment session (e.g., as described above, during a treatment planning session). For anatomically or biologically relevant radiation delivery metrics, the real-time radiation delivery metrics may be superimposed over anatomical or biological data collected either before or during the treatment session, for example, CT and/or MRI images. The real-time value of a radiation delivery metric may be displayed as a function of time over the treatment session, which may allow the operator to monitor changes in the metric during treatment as well as compare the real-time value of the metric with the expected value of the metric. This may also help the operator to determine whether radiation delivery is "on track" to delivering the cumulative radiation dose by the end of the treatment session as specified by the treatment plan.

In some variations, a radiotherapy system controller may comprise a processor that is configured to accumulate the data from the plurality of sensors and to use the sensor data to calculate the fluence (i.e., radiation fluence and/or radiation energy fluence) emitted by the linac that is directed to the patient and/or to calculate the dose delivered to the patient. For example, a radiotherapy system imaging system (that may be coupled to the rotatable gantry or a second gantry adjacent to the rotatable gantry) may comprise one or more optical cameras, sensors/imagers and/or may comprise a CT imaging system (e.g., having a kV radiation source and a kV detector located across from the kV radiation source), a MM imaging system (including MM sensors), and/or ultrasound system (including ultrasound transducers). Some radiotherapy systems may also comprise one or more arrays of PET detectors. The PET detectors may be located on the rotatable gantry to which the linac is mounted, or on a separate gantry that may or may not be rotatable. The therapeutic radiation source (e.g., a linac) may comprise its own controller that receives commands/instructions from the radiotherapy system controller, and/or an ionization chamber (i.e., ion chamber or dose chamber) and/or any radiation-sensing detectors disposed within the radiation beam path. Characteristics of the radiation emitted by the linac, such as pulse frequency, pulse width(s), pulse magnitude or variation in energy intensity level, duty cycle, numbers of pulses, etc. may be obtained from the linac controller and/or linac dose monitor and/or ionization chamber and/or a MV detector and/or any other radiation detector located in the beam path of the linac (e.g., directly across from the linac or directly in front of the linac within the linac beam). Radiotherapy systems may comprise motion and/or position sensors located throughout the system that may be configured to detect the motion and/or position of the gantry (from which the motion and/or position of the therapeutic radiation source mounted on the gantry may be calculated), the motion and/or position of the leaves of the MLC, the motion and/or position of the jaws (and/or any other beam-shaping component), and may transmit this data to the controller for calculating the radiation delivery metrics and graphics described herein. Gantry motion and/or position may be detected by motion and/or position sensors, and/or digital inclinometers and/or accelerometers, and/or one or more encoders that detect the relative positions of one or more rotor elements in a rotatable ring (e.g., drum) of the gantry and one or more stator elements in a stationary frame of the gantry. Radiotherapy systems may comprise one or more sets of jaws disposed in the radiation beam path of the linac, where the size and shape of the aperture between the jaws (e.g., the space and/or distance between jaw boundaries or edges) may be determined or measured based on position and/or motion sensors associated with the jaws. Alternatively or additionally, the size and shape of the aperture and/or the position of the jaws may be fixed or set to a predetermined configuration, and that configuration may be stored in the radiotherapy system controller memory. Dynamic multi-leaf collimators (MLC) of a radiotherapy system may also comprise one or more position and/or motion sensors, and the data from those sensors may be used by the controller to determine the size and shape of the MLC opening. Each leaf of the MLC may have a corresponding position and/or motion sensor. In a system comprising a dynamic binary MLC, data from the position and/or motion sensors may be transmitted to the system controller, which may aggregate the position and/or motion data of all the MLC leaves to determine the overall size and shape of the MLC opening. Examples and details of various types of radiotherapy systems are described in U.S. patent application Ser. No. 15/814,222 filed Nov. 15, 2017 and PCT Appl. Ser. No. PCT/US2018/025252 filed Mar. 29, 2018, the disclosures of which are hereby incorporated by reference in their entirety.

The radiotherapy system controller may be configured to receive data from one or more of the sensors or detectors described above and to calculate radiation fluence (i.e., radiation energy fluence) emitted to the patient and/or dose delivered to the patient using the sensor or detector data. For example, the radiation fluence emitted to a patient may be calculated using data from the linac controller and/or ionization chamber and/or MV detector located directly across from the linac, position and/or motion sensors associated with the jaws, position and/or motion sensors associated with the leaves of the MLC. Optionally, radiation fluence may also be calculated using imaging data (e.g., imaging data and/or images from one or more of PET detectors, X-ray detectors, MM detectors, ultrasound transducers, and/or optical cameras or imagers) from the imaging system. The radiation dose delivered to a patient may be calculated using, for example, a convolution superposition dose calculation algorithm which applies a beam energy deposition kernel (modeled for the therapy beam during beam commissioning) and the Total Energy Released per Unit Mass (TERMA) in the patient which may be computed by tracing incident energy fluence on the patient through a density or electron density map representing the patient. The energy fluence may be calculated as a product of beam energy and beam fluence. The density or electron density map may be calculated by anatomical imaging data from the imaging system (e.g., imaging data and/or images from one or more of PET detectors, X-ray detectors, MM detectors, ultrasound transducers, and/or optical cameras or imagers, and/or one or more images used for treatment planning), and/or data from the position and/or motion sensors associated with the gantry, and/or data from the linac controller and/or ionization chamber, and/or MV detector located directly across from the linac, and/or data from the position and/or motion sensors associated with the jaws, and/or data from the position and/or motion sensors associated with the leaves of the MLC. Optionally, radiation dose delivered to the patient may be calculated using a dose calculation matrix (i.e., a matrix that maps radiation fluence values to dose values at a set of pre-selected regions or voxels in the patient), imaging data from the imaging system, and a radiation-firing matrix (i.e., a matrix that designates the conversion from imaging data to a fluence map) generated during treatment planning. The calculated fluence and/or dose levels may be stored in a controller memory, and the generated graphic(s) may reflect cumulative values of fluence and/or dose, and/or real-time (e.g., nearly instantaneous) values of fluence and/or dose, as described herein.

Methods

In some variations, the range of acceptable radiation delivery metric values may be calculated for one or more delivery metrics based on the parameters of the treatment plan. A treatment plan may include a fluence map that specifies the amount of radiation (e.g., intensity level, energy level) to be applied to the patient, according to the location(s) of the target region(s) and/or organs at risk (OARs). A fluence map may comprise a beamlet pattern and/or beamlet intensities to be applied to the patient during a treatment session. In some variations, the fluence map may be segmented into radiotherapy system component configurations and/or instructions (by the treatment planning system and/or the radiotherapy system). One or more of the radiation delivery metrics described herein may be calculated based on the fluence map and/or the radiotherapy system component configurations and/or instructions as specified by the segmented fluence map. For example, any of the methods described herein may comprise calculating a dose-volume histogram for one or more target regions or volumes of interest using images of the patient (e.g., one or more treatment planning CT and/or MRI images) and the segmented fluence map. For each target region, the controller (e.g., a processor of the controller) may calculate the radiation fluence emitted to the target region based on the radiation beam output by the linac (or any therapeutic radiation source), the size and shape of the radiation-transmitting aperture of the beam-shaping components (e.g., the MLC and/or jaws), and the location of the linac relative to the target region when the beam is emitted, which parameters may be specified by the segmented fluence map. A dose level at that target region may be calculated based on the radiation fluence emitted by the linac, and the absorption of the emitted fluence by any intervening anatomical structures (e.g., bones, high-density tissue, any implants, etc.) between the linac and the target region, as well as the radiation absorption properties of the tissue at the target region. For example, a dose level for each volumetric proportion of a target region may be calculated using a treatment planning image (or images), the treatment plan fluence map, and a dose calculation matrix that maps fluence values to dose values at one or more pre-selected regions in the patient (e.g., sampling points or voxels within a target region).

The dose level delivered to regions or proportions of the target region (e.g., target tissue or planning target volume) may be represented in the form of a histogram (i.e., a dose-volume histogram) that plots dose units per (volumetric) proportion of the target region. In some variations, a family of DVH curves may be calculated based on treatment planning parameters (e.g., the fluence map) and by varying the location of the tumor tissue within the target region. An upper DVH curve (or maximum dose distribution) and a lower DVH curve (or minimum dose distribution) may be extracted from the family of DVH curves by, for example, selecting the right-most DVH curve and the left-most DVH curve, respectively. Additional details regarding the calculation of bounded DVH curves are included in co-pending U.S. patent application Ser. No. 16/016,272, filed Jun. 22, 2018, which is hereby incorporated by reference in its entirety. The bounded DVH curve(s) may be stored in the memory of a radiotherapy system controller and displayed alongside real-time DVH curves that may be calculated using linac output data (e.g., pulse intensity, duration, frequency, dose) from the linac controller and/or ionization chamber, and/or MV detector located directly across from the linac, linac location data when firing radiation pulses (e.g., from gantry position and/or motion sensors), MLC leaf configuration (e.g., from MLC leaf position and/or motion sensors), imaging data (e.g., acquired from PET detectors, X-ray detectors, etc.), and/or any adjustments in fluence in response to patient and/or tumor changes during the session (e.g., motion artifacts, etc.).

In some variations, the fluence map from a treatment plan may be segmented and discretized into radiation firing intensity values per MLC leaf per gantry firing position for various patient platform positions. A graphic representing radiation delivery may comprise a plot of radiation firing intensity levels (e.g., magnitude of the radiation applied, and/or duty cycle and/or frequency and/or width of radiation pulses, etc.) for each open MLC leaf at each linac position about the patient (e.g., gantry firing angles) as specified by the segmented fluence map. A first plot of radiation firing intensity levels for each open MLC leaf at each linac position (and optionally, for each position of the patient platform relative to the linac position) may be calculated based on the segmented fluence map that has been generated by the treatment planning system. This first plot may represent the ideal or target radiation delivery profile. Additional plots of radiation firing intensity levels for each MLC leaf may be calculated based on data acquired during the treatment session, including, but not limited to MLC leaf motion and/or position sensor data, linac output data (e.g., from a ionization chamber or a dose chamber and/or MV detector located directly across from the linac), and linac position data. These additional plots may be generated at pre-determined time points or control points (e.g., checkpoints) during a treatment session, as described herein. Optionally, radiation firing intensity levels for each MLC leaf at each linac position may be calculated for each patient platform position, for example, as the patient platform steps a patient through a gantry bore. While the examples and variations described herein may depict the measurement and evaluation of radiation delivery at specified time points, it should be understood that similar measurements and evaluations may be conducted at specified control points and/or checkpoints, as may be desired.

In some variations, a graphic representing radiation delivery may comprise numerical values of one of more plan quality indices (PQIs) for each of the target regions or volumes-of-interest. A PQI represents the degree to which a treatment plan fluence map provides sufficient radiation to tumor regions while sparing or limiting radiation exposure to organs-at-risk (OARs). As patient and/or tumor regions conditions change during a treatment session, the fluence map prescribed by a treatment plan may become more (or less) effective at emitting radiation to tumor regions. Examples of PQIs that may be monitored during a treatment session may include mean dose levels in a radiation target region, volumetric coverage of a 95% (V95) or 100% (V100) dose level Reference over a target region (e.g., if dose objective for a target region is 2 Gy, the V100 PQI specifies the volumetric proportion of the target region that has received a dose of at least 2 Gy), and/or maximum dose level in an OAR. PQI values (e.g., a range of acceptable PQI values calculated based on patient and/or tumor regions at the time of treatment planning and/or a range of PQI values that have been reviewed and approved by a clinician) may be displayed along with PQI values calculated using data acquired during the treatment session, including, but not limited to MLC leaf motion and/or position sensor data, jaw motion and/or position sensor data, gantry position and/or motion sensors (e.g., collecting gantry angle and/or speed data), and/or couch position and/or speed sensors, linac dose rate data (e.g., from a ionization chamber or a dose chamber and/or MV detector located directly across from the linac).

A radiotherapy system may calculate a plurality of radiation delivery metrics and display a plurality of graphical representations of those radiation delivery metrics over time. Some radiation delivery metrics may be calculated based on radiation fluence data while other radiation delivery metrics may be calculated based on absorbed dose data. Sensors collecting data about the number of particles and quantity of energy being released (e.g., linac pulse sensor data optionally combined with gantry and leaf sensor data) may then be correlated with positional information are used to calculate fluence which may be used to calculate the absorbed dose based on the medium to which the energy is being applied. Similarly, sensors collecting and reporting absorbed dose data (e.g. MV dosimetry sensor placed opposite the linac) can be used to directly provide radiation delivery metric calculations when correlated with radiotherapy planning artifacts like segmented volume and positional data from the radiotherapy device's positional sensors. Radiation fluence may be measured using, for example, a MV detector located across from a therapeutic radiation source such as a linac, and the fluence measurements may be combined with anatomical data (e.g., from CT images, anatomical structure data including geometry, density of anatomical structures, attenuation coefficient of anatomical structures, etc.). Examples of radiation delivery metrics and corresponding graphical representations are described below.

While the radiation delivery metrics and graphical representations described herein have been described in the context of an emission-guided radiotherapy system (where therapeutic radiation is applied according to positron annihilation photon emissions from a PET tracer injected into a patient), it should be understood that these delivery metrics and graphical representations may be used with any radiotherapy system and/or radiation delivery methods to monitor and track the progress of a radiation delivery session (e.g., a treatment session and/or a QA session). For example, the radiation delivery metrics and graphical representations described herein may be used with a radiotherapy system that applies therapeutic radiation according to imaging data acquired during a treatment session while the therapeutic radiation source is activated (i.e., beam on). Such systems may include radiotherapy systems that apply therapeutic radiation according to real-time acquired MRI sensor data (e.g., sub-samples in k-space) and/or real-time acquired X-ray detector data (e.g., 2-D projection X-ray data from kV and/or MV X-ray detectors). The delivery metrics and graphical representations may also be used with any image-guided radiotherapy systems, utilizing any treatment delivery modality such as IMRT (helical intensity modulated, VMAT, dynamic arc, step-and-shoot IMRT or sliding window IMRT with a 2D modulation) or 3-D conformal delivery with single or multiple static gantry, couch, jaws and MLC settings, or 3-D conformal arc delivery, and any radiation source mounting configurations, such as C-arm, helical, robotic or static multiple source arrangement of radiation sources placed around the patient target area.

Real-Time Dose-Volume Comparisons

One type of radiation delivery metric may comprise radiation dose data over volumetric quantities. Graphics that represent dose-volume data may include plots of dose data across patient or phantom volumes and/or dose data superimposed over patient structures or phantom regions. For example, graphics representing dose-volume comparisons may include isodose contours, dose-volume histograms (DVHs), and dose gradient images. While these radiation delivery metrics are typically calculated and graphically represented at the end of a treatment session, the methods described herein comprise calculating these metrics and generating corresponding graphics in real-time, concurrent with radiation delivery. Furthermore, the generated graphics may include the real-time values of the dose-volume metrics as well as the pre-treatment values of the same dose-volume metrics calculated based on the treatment plan and planning parameters. For example, before the treatment session, the value of the dose-volume delivery metrics may be calculated at each pre-determined time point of the treatment session for each target region or volume-of-interest. The dose delivered at a particular time point may be calculated using anatomical image data (e.g., data from the imaging system), linac location data (e.g., data from gantry position and/or motion sensors), linac radiation emission data (e.g., from the linac controller and/or ionization chamber and/or MV detector located directly across from the linac), jaw aperture data (e.g., data from jaw position and/or motion sensors), and/or MLC aperture data (e.g., data from MLC leaf position and/or motion sensors). Such sensor and/or detector data may be acquired just before the dose calculation. Optionally, the dose delivered at a particular time point may be calculated by multiplying a dose calculation matrix with a fluence emitted at that time point. A dose-volume computation may further comprise calculating the fraction of a ROI or target region volume that has received at least the requested dose level D (which may be determined by counting the number of voxels that have received at least a dose level D, and diving this number of voxels by the total number of voxels comprising the entire volume of the ROI or target region). Various dose-volume metrics may be derived from the dose levels over a volume of tissue. For example, some methods may comprise generating a graphic that represents cumulative delivered dose (e.g., over the entire treatment session, and/or summing delivered dose from the start of the treatment session until the current time point) and/or generating a graphic that represents the dose delivered over an interval of time at or around the particular time point. The real-time dose-volume delivery metric may be overlaid with (or otherwise compared with) a dose-volume delivery metric value calculated based on treatment planning patient and system parameters to identify any discrepancies between the actual radiation delivery progress with the planned radiation delivery progress. In one example, to calculate a conformity index (which may be a ratio of V100/PTV, where V100 is the volume in cc covered by the isodose surface corresponding to a 100% dose prescription, and PTV is a planning target volume in cc), the radiotherapy system may be configured to calculate the dose in the vicinity of the target than includes all of the 100% isodose surface, calculate the number of voxels that have their doses equal to at least the 100% prescription dose, and then divide this number of voxels by the number of voxels comprising the PTV. In another example, to calculate a dose gradient index, the radiotherapy system may be configured to calculate a ratio of V50/V100 or V50/PTV, where the V50 and V100 are calculated as the number of voxels having at least 50% and 100% prescription dose, respectively.

In some variations, the planned dose-volume delivery metric value at a particular time point during a treatment session may be calculated by scaling the dose-volume delivery metric value of the entire session by the proportion of time that has elapsed. The pre-calculated value of the dose-volume delivery metrics (i.e., expected value of the metric) at each time point or control point may include the amount of dose delivered at the time point (e.g., may be cumulative dose and/or dose delivered at that time point), and the configuration of the beam-shaping components (i.e. MLC leaf configuration and/or jaw configuration) at that time point. Additional sensor data may be incorporated as well to provide additional inputs into the dose reconstruction (e.g., MV dosimetry sensor data, such as the intensity of the transmitted radiation at each pixel, correlated with positional and/or motion data from any of the radiotherapy system sensors described above). For example, calculating the dose delivered to a target region using imaging data acquired during the treatment session may be more accurate than calculating the dose using treatment planning imaging data. This pre-calculated or expected dose-volume delivery metric may be applied over, or calculated using, the current control point's associated volume of interest data (e.g., CT slice, radiation therapy structure set, and/or conceptual volume definitions). This may provide, for example, a calculation of the real-time cumulative radiation dose correlated with volume from the start of delivery to the current point in time. Examples of different graphics representing real-time dose-volume radiation delivery metrics as compared to expected dose-volume radiation delivery metrics are described below.

Isodose Contour Comparison

Isodose contours may be used to display how much dose is expected to be delivered to a given volumetric region during a radiation treatment session. FIG. 1A depicts one example of a graphic that comprises expected isodose contours vs. real-time isodose contours calculated based on data acquired during a treatment session. These isodose contours are superimposed over an anatomical image of the patient (windowed to show contrast). The graphic may be updated continuously and/or at pre-determined time points during the treatment session to reflect a build-up of the isodose contours over time. Real-time isodose contours may be generated by calculating a 3-D or 2-D dose distribution or profile over a target region by calculating the delivered dose at each sampling point (e.g., voxel or pixel) in the target region. The delivered dose to a target region may be calculated as described above, for example, using data from the linac controller and/or ionization chamber, and/or MV detector located directly across from the linac, position and/or motion sensors associated with the beam-shaping components (e.g., jaws, MLC leaves), position and/or motion sensors associated with the gantry and/or linac, imaging data from the imaging system of the target region (e.g., PET data, CT data, etc.). The controller processor of the radiotherapy system may be configured to project the delivered dose over the target region or volume-of-interest. Optionally, some methods may comprise calculating delivered dose profiles by multiplying a dose calculation matrix with a fluence emitted at that time point. In some variations, the fluence may be calculated by multiplying the radiation-firing matrix with acquired imaging data (e.g., PET emission data). After a 2-D or 3-D dose distribution or profile is generated, isodose contour lines may be generated by tracing and/or connecting portions of the target region that satisfy a user-defined dose criteria, such as having the same dose level or being greater than or less than the selected dose level. In some variations, the isodose contours or lines may be generated for discrete dose levels. The isodose contours or lines may be overlaid with a CT or MRI (or any anatomical) image, and optionally in combination with a PET image. FIG. 1A depicts an example of a graphic comprising isodose contours or lines. The dashed isodose contour line (102) represents the planned 95% isodose (D95%$_{PLAN}$) at each time point, the dotted isodose contour line (104) represents sensor-derived 95% isodose (D95%$_{REAL-TIME}$) at each time point. The solid contour line (106) may represent any target volume or region-of-interest, such as the planning target volume or PTV (i.e. gross tumor volume, any surrounding tissue may be diseased, and any setup, imaging and motion uncertainties.). The rate at which the 95% isodose region covering the tumor changes during the radiation delivery from time point $t_0$ (no delivered dose) to time point $t_1$ (partially delivered dose) to time point $t_2$ (completely delivered dose), may be represented by the region enclosed by the D95%$_{REAL-TIME}$ contour. This may be updated in real-time during radiation delivery and as delivery progresses may increase in size and converge with the PTV contour 106 (e.g., approaching the region described by the D95%$_{PLAN}$). In some variations, the graphic may be animated to depict the accumulation of radiation dose represented by the isodose contours over the duration of the treatment session, providing a motion tween (i.e., animation vector) from one derived state to the next. This may provide a volumetric vector by which the operator may evaluate the current progress and accuracy of the radiation delivery. The operator may select one or more levels at which they wish to display the isodose value. For example, the operator may select the 50% dose isodose, which represents the volume of the region that has received at least 50% of the maximum point dose level. The operator may additionally select a range for the given isodose level at a specific time point $t_0$ create delivery verification checkpoints, which can be represented as shaded regions (108) representative of the acceptable range at a given time point during radiation delivery, as shown in FIG. 1B. Alternatively or additionally, the real-time isodose contour may be generated and displayed together with the time-dependent plan isodose at a time t. By visualizing how close the real-time isodose contour is to the expected plan isodose contour at time t, the operator may track the accuracy of delivery (i.e., the real-time isodose may closely approximate the expected (planned) isodose during radiation delivery).

Dose Gradient Buildup

Alternatively or additionally, graphics that represent the build-up of radiation dose, fluence, and/or cumulative radiation dose delivered may comprise dose gradients overlaid on anatomical images. Anatomical images may be CT and/or MM images acquired before the treatment session (e.g., during treatment planning and/or treatment plan quality assurance or validation sessions), or at the start of the treatment session (e.g., before the therapeutic radiation source is activated and/or applies the first radiation pulse). Dose gradients calculated based on real-time acquired data may be used to generate a graphic that represents the cumulative build-up of the dose distribution or profile over time. FIG. 1C depicts one example of a graphic depicting dose gradients superimposed over anatomical image(s) of the patient. Real-time dose gradients may be generated during a treatment session by calculating a 2-D or 3-D dose distribution or profile over a target region by calculating the delivered dose at each sampling point (e.g., voxel or pixel) in the target region. The delivered dose to a target region may be calculated as described above, for example, using data from the linac controller and/or ionization chamber, and/or MV detector located directly across from the linac, position and/or motion sensors associated with the beam-shaping components (e.g., jaws, MLC leaves), position and/or motion sensors associated with the gantry and/or linac, imaging data from the imaging system of the target region (e.g., PET data, CT data, etc.). The controller processor of the radiotherapy system may be configured to project the delivered dose over the target region or volume-of-interest. Optionally, some methods may comprise calculating delivered dose profiles by multiplying a dose calculation matrix with a fluence emitted at that time point. In some variations, the fluence may be calculated by multiplying the radiation-firing matrix with acquired imaging data (e.g., PET emission data). After the 2-D or 3-D dose distribution or profile is generated, a dose gradient plot may be generated by plotting the dose value per voxel or pixel where the intensity of a voxel or pixel represents the delivered dose level to that voxel or pixel. For example, a higher pixel intensity may correlate with a higher delivered dose level. The dose gradient plot may be overlaid with a CT or MRI (or any anatomical) image, and optionally in combination with a PET image and/or an outline of the target region (e.g., planning target volume, tumor region, OAR, etc.). Contour lines may be drawn around to regions with delivered dose, for example, to accentuate the boundaries or edges of regions where the delivered dose meets or exceeds a threshold value. Cumulatively, if radiation delivery is proceeding according to the treatment plan, the area(s) of higher dose levels will expand (e.g., see expansion of regions receiving dose from time points $t_0$, $t_1$, $t_2$ in FIG. 1C). Alternatively or additionally, a radiotherapy system controller may be configured to generated dose gradients by calculating the dose in the patient and calculating the dose gradient at every point in or near the target region. One variation of a real-time dose calculation method may uses a fast-dose calculation algorithm which uses the total energy released per unit mass (TERMA) at and near the target region, which in turn is computed from the energy fluence incident on the patient at every gantry firing position and every beam slice (or patient platform position). The energy fluence for every firing position may be calculated by calculating the beam energy spectrum weighted fluence, which may in turn be calculated based on the MLC leaves that were opened at a particular gantry firing position and the amount of radiation (e.g., number of MU) emitted at this gantry firing position. Optionally, the graphic may also comprise the planned dose gradient or distribution against which the real-time dose gradients may be compared with optional acceptable ranges at a delivery verification checkpoint, as depicted in FIG. 1D. In one variation, the planned dose gradient or dose profile (and/or the range of acceptable dose gradients or profiles) may be generated during a treatment planning session by shifting a tumor (e.g., tumor tissue) to multiple locations within the target region (e.g., planning target volume), calculating a dose gradient or profile for each of the shifted tumor locations to generate a family of dose gradients or profiles. The dose gradient or profile with the largest area or volume in the family may be upper boundary of a range of acceptable dose gradients, and the dose gradient or profile with the smallest area or volume in the family may be a lower boundary of the range of acceptable dose gradients. The planned dose gradient or dose profile (and/or the range of acceptable dose gradients or profiles) over an entire treatment session may be proportionally scaled for each time point or checkpoint and reflected in the graphic. For example, the area or volume encompassed by the planned dose gradient (and/or the range of acceptable dose gradients) may be correspond with the scaled by 10% (i.e., 1/10 of the total area or volume) for a checkpoint that is 10% the duration of the entire treatment session, 25% (i.e., 1/4 of the total area or volume) for a checkpoint that is 25% the duration of the entire treatment session, etc. Alternatively or additionally, the planned dose gradient or dose profile (and/or the range of acceptable dose gradients or profiles) over an entire treatment session may be non-linearly scaled for each time point or checkpoint and reflected in the graphic. For example, the expected dose profile at a first time point or checkpoint (e.g., a first control point, a first beam station) may specify that 10% of the target region (e.g., PTV) will have received 10% of the total fluence delivered to the target region. The expected dose profile at a second time point or checkpoint (e.g., a second control point, a second beam station) may specify that a total of 25% of the target region (e.g., PTV) volume will have received 15% of the total fluence delivered to the target region (e.g., there may be additional volume visible but less fluence to be delivered). The expected dose profile at a third time point or check point (e.g., a third control point, a third beam station) may specify that a total of 30% of the target region (e.g., PTV) volume will have received 50% of the total fluence delivered to the target region (e.g., there may be a small amount of volume visible but a large amount of fluence to be delivered here because it may be the most active part of the tumor). Alternatively or additionally, in some variations (e.g., intensity-modulated radiation therapy), the planned dose gradient or dose profile for each time point or checkpoint may correspond with the dose delivered when the radiotherapy system is configured according to the segmented planned fluence map. At each checkpoint, the radiotherapy system controller may generate graphics displayed on a monitor or screen and/or a notification (e.g., a visual and/or audio notification) to the operator if any portion of the delivered dose extends outside of the boundary (or boundaries) of the acceptable dose range by a selected threshold. Alternatively or additionally, the planned dose gradient or dose profile (and/or the range of acceptable dose gradients or profiles) over an entire treatment session may be displayed in the generated graphic, without any intermediate dose gradients or profiles.

Real-Time Dose-Volume Histogram

Figure 2B:
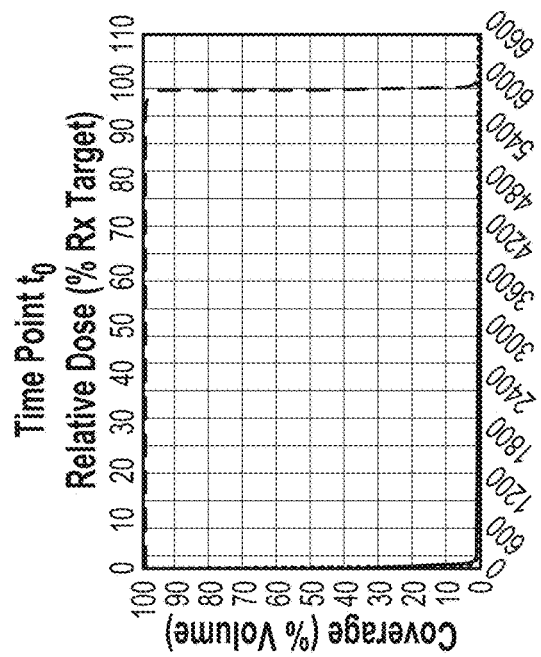
Figure 2C:
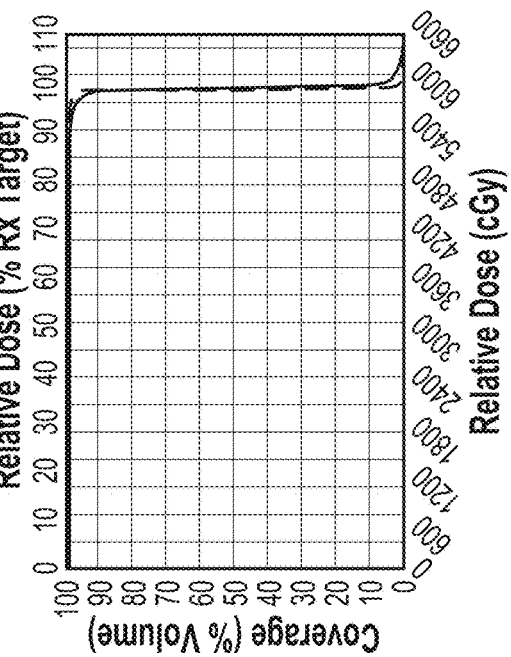

Alternatively or additionally, graphics that represent the build-up of radiation dose and/or cumulative radiation dose delivered in a two-dimensional plot may comprise one or more dose-volume histograms (DVHs). As described previously, planned or expected DVH values or curves may be calculated prior to treatment. In some variations, bounded DVH curves comprising an upper DVH curve and a lower DVH curve may be generated during a treatment planning and/or a treatment plan evaluation session and stored in the memory of the radiotherapy system controller. Bounded DVH curves may be generated as described above (i.e., by shifting or varying the location of tumor tissue within a target region and calculating the dose units/levels delivered to proportions of the target region for each of the shifted tumor tissue locations). DVH curves may be generated in real-time using data acquired during the treatment session. In some variations, the dose delivered at a particular time point may be calculated using anatomical image data (e.g., data from the imaging system), linac location data (e.g., data from gantry position and/or motion sensors), linac radiation emission data (e.g., from the linac controller and/or ionization chamber and/or MV detector located directly across from the linac), jaw aperture data (e.g., data from jaw position and/or motion sensors), and/or MLC aperture data (e.g., data from MLC leaf position and/or motion sensors). Such sensor and/or detector data may be acquired just before the dose calculation. Optionally, the dose delivered at a particular time point may be calculated by multiplying a dose calculation matrix with a fluence emitted at that time point. The dose units/levels per volumetric proportion of the target region may be plotted as a DVH or DVH curve. Some methods may comprise calculating planned or expected DVH at pre-determined time points or control points. Optionally, some methods may comprise calculating a range of acceptable DVH variation at the pre-determined time points. During radiation delivery, the DVH values calculated based on real-time acquired data may be plotted on the same grid as the expected or planned DVH values or curves (e.g., bounded DVH curves). FIG. 2A depicts one example of a DVH graphic that depicts the planned DVH curve for a target region, the intermediate DVH curves calculated during the treatment session (e.g., at time point $t_1$), and the planned DVH curve at the given time point during the treatment session. The dashed, planned DVH curve represents the final dose-volume histogram desired at the end of the treatment session. The solid DVH curve ($PTV_{REAL-TIME}$) represents the dose-volume accumulation after a partial delivery of the planned radiation delivery, and the dotted DVH curve ($PTV_{PLAN}$) represents the dose-volume accumulation expected at the given time point. FIG. 2B represents a variation of the DVH build-up that depicts the delivery verification check points at each time point. For each time point, the planned DVH curve is displayed along with upper and lower bound defining an acceptable range of DVH variation, i.e., a bounded DVH calculated based on the treatment plan, as described above. The operator may, for example, confirm during the treatment that radiation delivery is proceeding toward the cumulative planned DVH, as well as staying within the acceptable range of DVH values.

Real-Time Beam Firing Patterns

In order to display the firing pattern of a helical or arc delivery, a sinogram of gantry position and leaf position may be used to display a specific intensity of delivered radiation from each leaf-gantry position. One variation of sinogram may comprise a map that specifies the configuration of individual MLC leaves for each firing position (e.g., gantry firing angle). A sinogram may be displayed to a monitor along with any of the other graphics and/or delivery metrics described herein. In some variations, the sinogram may be calculated using MLC leaf position sensor data, linac position sensor data (e.g., linac firing location corresponding to a particular MLC configuration), and/or linac ionization chamber or dose chamber data and/or MV detector data. This sinogram may be an indication and/or confirmation that the MLC leaves are opening and closing during radiation delivery, and may optionally provide a visual or audio indicator if one or more MLC leaves are not moving at all (e.g., stuck in an open configuration or a closed configuration or any intermediate configuration or is outside of the expected range). For example, the radiotherapy system controller may be configured to detect whether an MLC leaf has an invalid position at a particular control point, and if an MLC leaf is in an invalid position, the controller may generate a visual and/or audio notification or alert to the operator. In some variations, an invalid MLC leaf position may be detected by comparing MLC leaf positions at a particular gantry firing position and/or patient platform position with the MLC leaf positions as specified by a segmented planned fluence map (i.e., the fluence map generated during treatment planning). Deviations from the MLC leaf positions as specified by the segmented planed fluence map may be detected or flagged as invalid MLC leaf positions. Alternatively or additionally, some radiotherapy systems may be configured to calculate a fluence map during the treatment session (i.e., a real-time calculated fluence map) and may also be configured to segment the calculated fluence map in real-time (e.g., biologically-guided radiotherapy or BGRT, emission-guided radiation therapy or EGRT, and/or image-guided radiation therapy or IGRT), an invalid MLC leaf position may be detected by comparing the fluence (e.g., radiation intensity) emitted through that leaf and comparing the fluence emitted (or dose delivered) with the real-time calculated fluence map. If the emitted fluence through a MLC leaf exceeds the fluence level specified by the real-time calculated fluence map (e.g., is greater than the highest fluence level specified by the fluence map) and/or exceeds predetermined fluence thresholds, then the radiotherapy system may generate a notification or indicator that the MLC leaf is in in an invalid position.

2D Real-Time Sensor-Derived Sinogram Representations

Figure 3A:
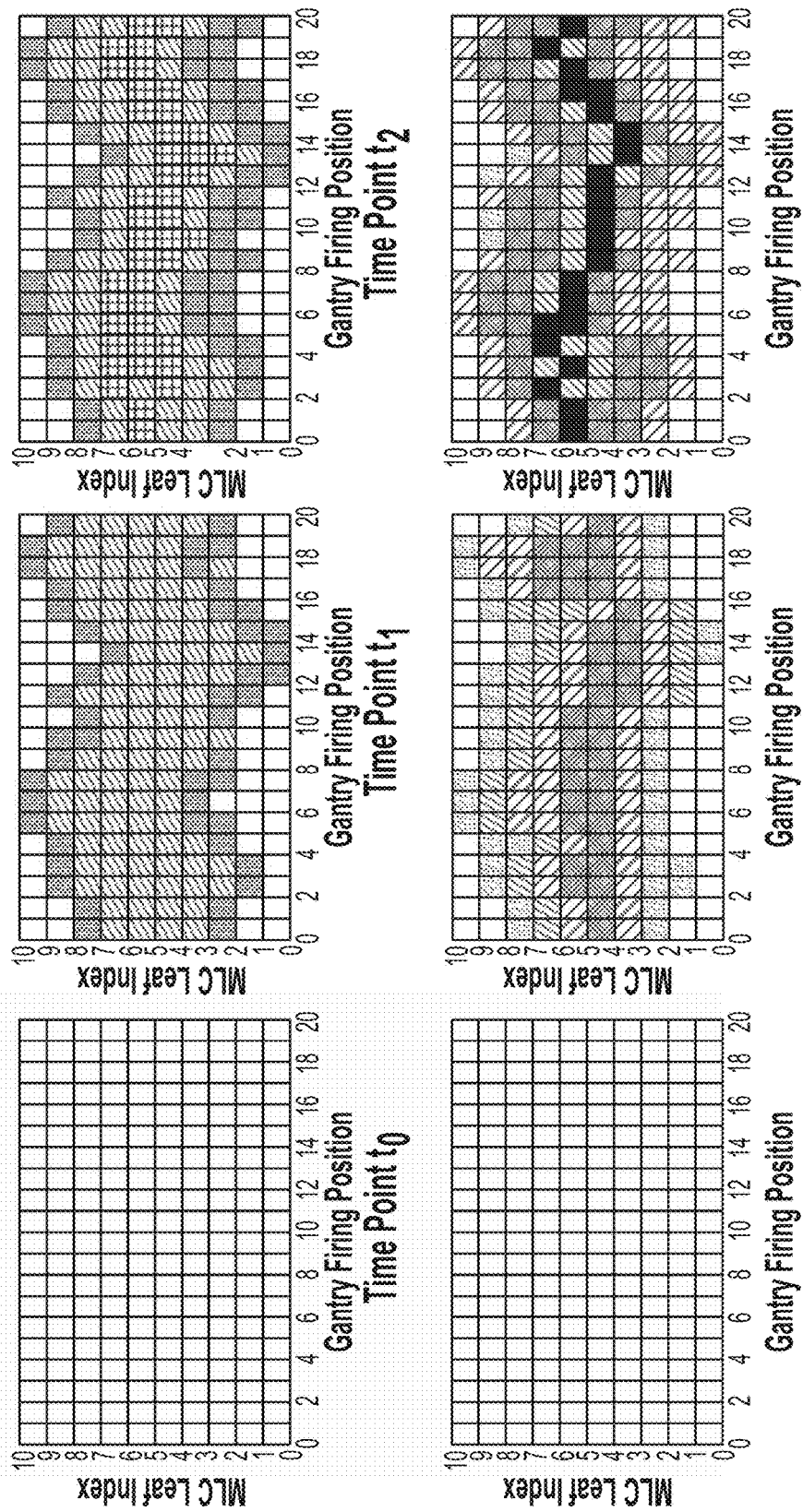
FIG. 3A depicts one example of a graphical representation comprising sinogram data bitmasks.

In some variations, a real-time reconstruction of a beam firing pattern graphic may be generated by combining sensor data at the time of radiation delivery with the original or planned expected pattern. Some graphics may comprise one or more visual indicators that represent real-time sensor-derived sinogram data. One variation of a graphic that represents sinogram data may comprise a first bitmask that displays acceptable ranges of the firing pattern within clinical (or planned) tolerances, and a second bitmask that displays the real-time sensor-derived firing pattern. FIG. 3A depicts an example of a graphic that depicts the planned sinogram bitmask (top row) and with the real-time MLC-leaf sensor-derived sinogram bitmask (bottom row) parallel to each other but on separate plots. Optionally, an acceptable range of firing patterns or sinogram values may be provided. The planned sinogram bitmask (top row of FIG. 3A) may be generated based on the MLC, linac, and/or gantry commands or instructions of a segmented fluence map. The fluence map may be the treatment plan fluence map (i.e., generated during a treatment planning session and/or treatment plan evaluation session), and/or may be a fluence map derived from multiplying imaging data (e.g., PET emission data) with a radiation-firing matrix. Generating a planned sinogram bitmask for a radiotherapy system with a binary MLC and a linac mounted on a rotatable gantry may comprise depicting the MLC leaf configuration for each leaf for each gantry firing position (i.e., whether a MLC leaf is open or closed) by marking a cell (or "bit") on the map as "open" if specified as such according to the segmented planned fluence map, and for each MLC leaf that is in the open configuration, depicting the intensity (or energy level) of the radiation emitted by the linac through that leaf by shading that cell (or "bit") with an intensity (and/or pattern with a spatial frequency) that correlates with the radiation intensity or energy emitted by the linac as specified by the segmented planned fluence map. This may be repeated for all of the time points or checkpoints specified in the treatment session. While the examples depicted herein may depict cells, pixels, and/or voxels shaded in (or filled with) various intensities, opacities or transparencies, and patterns in grayscale or black-and-white, it should be understood that in other examples, cells, pixels, and/or voxels may be shaded in (or filled with) various intensities, opacities or transparencies, and patterns in one or more colors (e.g., colorized).

The real-time, actual sinogram bitmask (bottom row of FIG. 3A) may be generated based on sensor and/or detector data from the position and/or motion sensors associated with the MLC leaves and/or gantry, and the data from the linac controller and/or linac ionization chamber and/or MV detector acquired during the treatment session. Generating a real-time sinogram bitmask that reflects the actual configurations of the MLC, gantry and/or linac may comprise depicting the MLC leaf configuration for each leaf for each gantry firing position as specified by the gantry position and/or motion sensor(s) by marking a cell (or "bit") on the map as "open" according to the sensor data of each MLC leaf, and for each MLC leaf that is in the open configuration, depicting the intensity (or energy level) of the radiation emitted by the linac through that leaf by shading that cell (or "bit") with an intensity (and/or pattern with a spatial frequency) that correlates with the radiation intensity or energy emitted by the linac as indicated by the linac controller and/or ionization chamber and/or MV detector. This may be repeated for all of the time points or checkpoints specified in the treatment session. While the examples depicted herein may depict cells, pixels, and/or voxels shaded in (or filled with) various intensities, opacities or transparencies, and patterns in grayscale or black-and-white, it should be understood that in other examples, cells, pixels, and/or voxels may be shaded in (or filled with) various intensities, opacities or transparencies, and patterns in one or more colors (e.g., colorized).

Figure 3B:
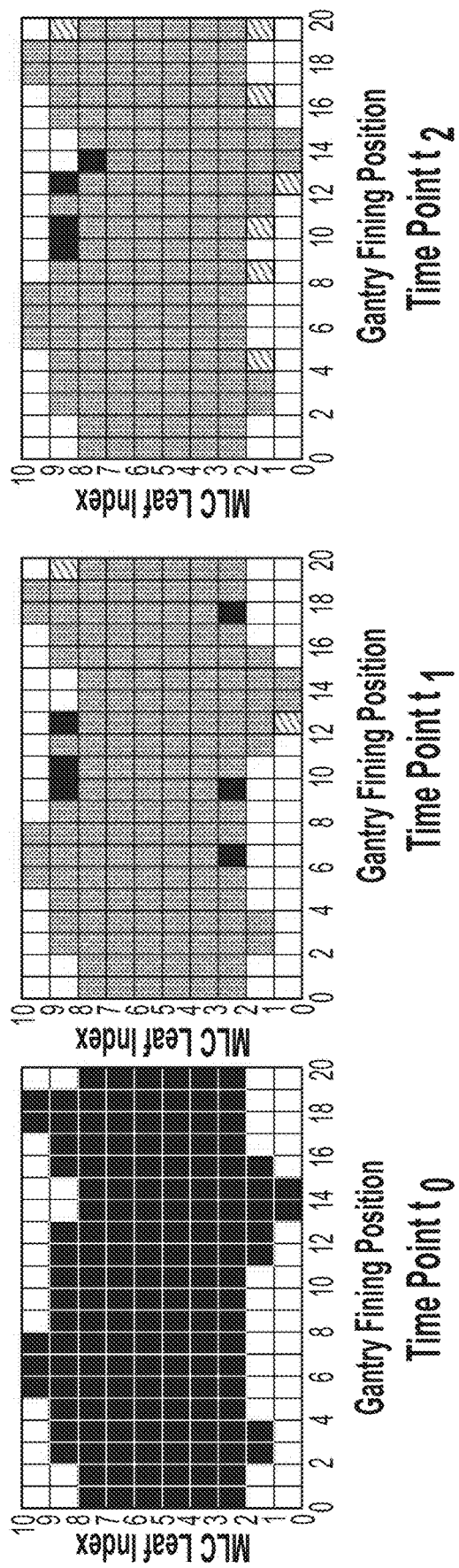
FIG. 3B depicts one example of a graphical representation comprising a sinogram data bitmask indicating an acceptable range of sinogram values.
Figure 3C:
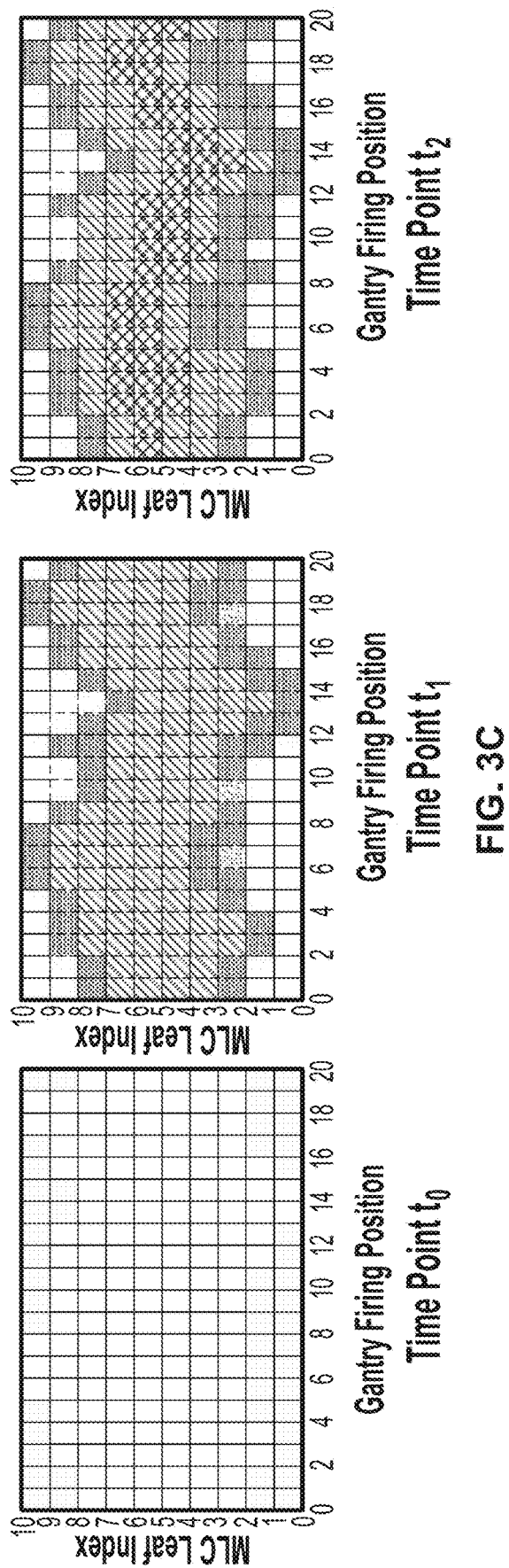
FIG. 3C depicts one example of a graphical representation comprising sinogram data bitmasks.
Figure 3D:
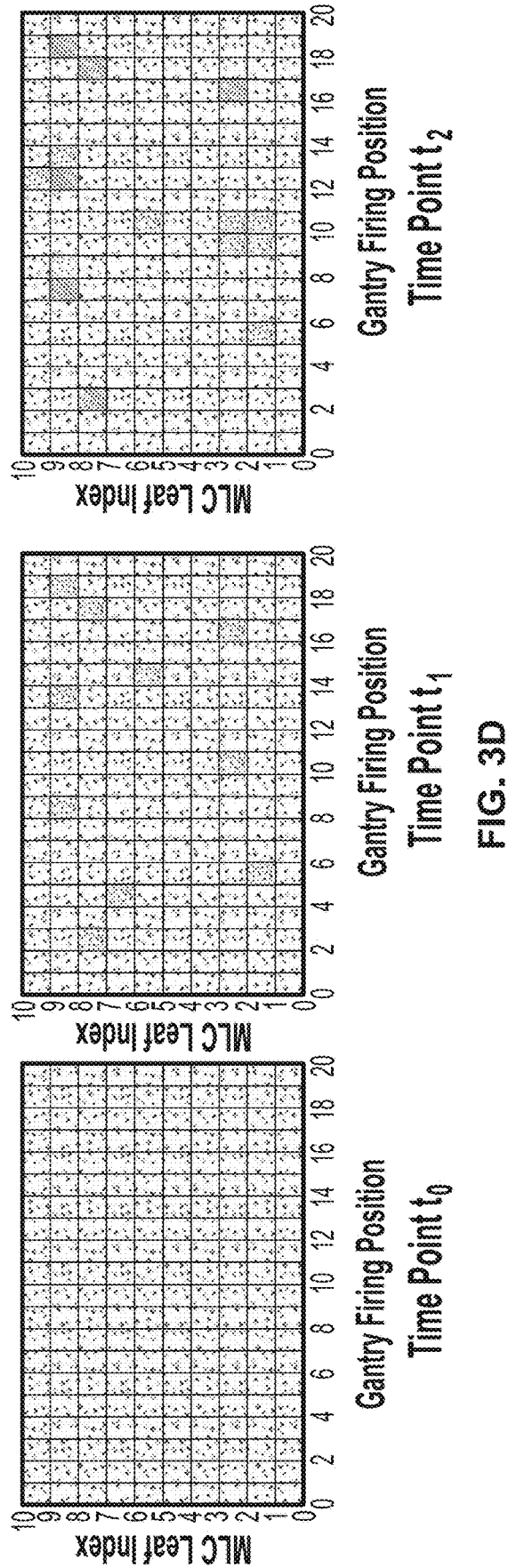
FIG. 3D depicts one example of a graphical representation comprising a sinogram data bitmask that indicates the difference between the real-time sensor-derived sinograms and planned sinograms.
Figure 3E:
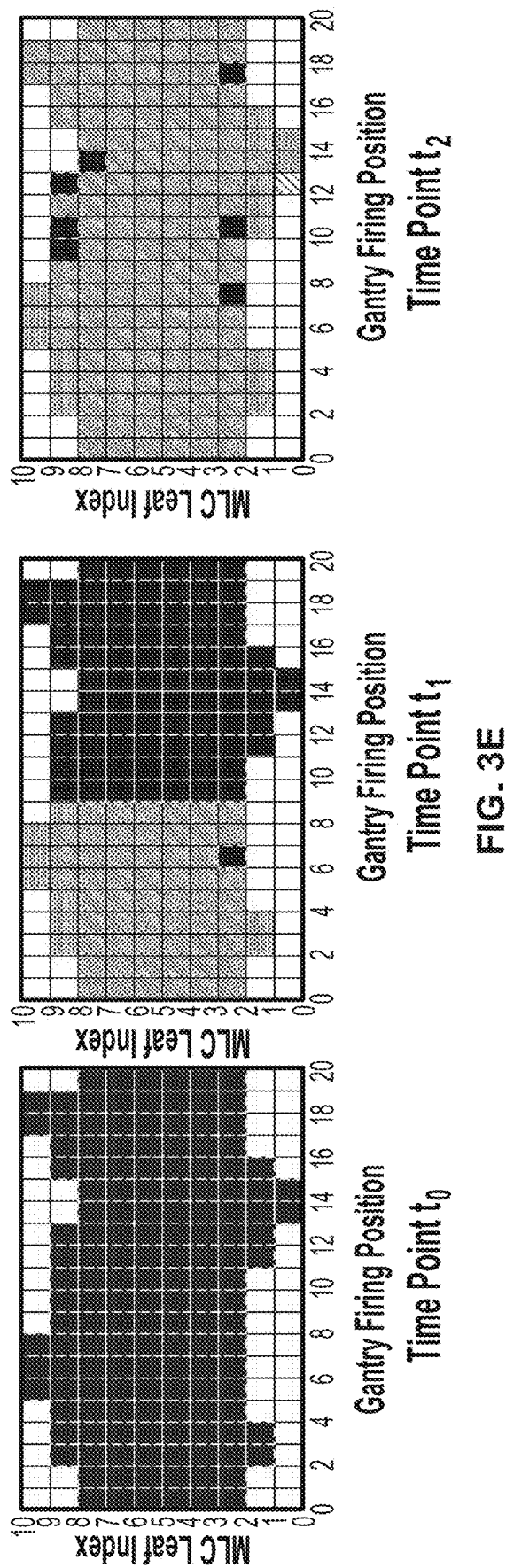
FIG. 3E depicts one example of a graphical representation comprising a sinogram data bitmask derived by collapsing sinogram data over a delivery session.

FIG. 3B depicts a bitmask that indicates the acceptable range of firing patterns or sinogram values for the treatment plan example of FIG. 3A. Cells (or "bits") on the bitmask may be marked with various visually-discernible indicia to indicate whether a particular MLC leaf is supposed to be opened or closed at a particular gantry firing position. For example, a bitmask may have a first shading for cells that represent MLC leaves that are to be intended to be open and/or permitted to be open (e.g., not intended to be open according to a segmented fluence map, but is within acceptable error margins or tolerances), and a second shading different from the first that represent MLC leaves that are intended to be closed and/or not permitted to be open (e.g., opening of such leaves would exceed an acceptable error margin or tolerance). A third shading different from the first two may represent MLC leaves that have opened (or are in the process of being opened) for each gantry firing position during the treatment session. The determination of whether a cell is to be marked with the third shading depends on sensor data from the position and/or motion sensors of the gantry and the MLC leaves. As an example, in FIG. 3B at time point $t_0$ prior to the emission of any radiation, the cells shaded with a first pattern, e.g., dark shading, indicates the MLC leaves that are to supposed to be (and/or permitted to be) open at the corresponding gantry firing position according to a segmented fluence map. At time point $t_1$ after radiation has been applied for at least 20 gantry firing positions, based on MLC leaf position and/or motion sensor data and gantry position and/or sensor data, cells in the bitmask may be shaded with a second pattern to indicate which of the MLC leaves shaded with the first pattern were opened at each gantry firing position during radiation delivery. Cells that were shaded with the first pattern, but where those corresponding MLC leaves were not opened during radiation delivery, may remain shaded with the first pattern. Cells that were not shaded with the first pattern at time point $t_0$ (i.e., corresponding to MLC leaves that should not be opened) may be shaded with a third pattern, e.g., light or no shading. The radiotherapy system controller (e.g., the processor of the controller) may be configured to identify MLC leaves that have not opened or closed according to the segmented fluence map and to generate a notification or visual alert (e.g., by different types of shading or blinking or fluttering) that the MLC leaves and/or gantry positions and/or motions have deviated from those specified in the segmented fluence map. For example, by time points $t_1$ and $t_2$, MLC leaves that have opened incorrectly (i.e., outside of what has been specified by the segmented fluence map) may be shaded with a fourth pattern, e.g., a hash-mark pattern, and MLC leaves that have not opened (i.e., remained closed even though the segmented fluence map indicates that they should have opened) may remain shaded with the first pattern. FIG. 3C depicts an example of a graphic that depicts the planned and real-time sinograms combined using opacity blending, where the real-time sinogram overlays the planned sinogram and a visual comparison can be made. Alternatively or additionally the difference between the real-time sensor-derived and planned sinograms may be displayed as its own sinogram. FIG. 3D depicts an example of a graphic that depicts the difference between the real-time sensor-derived sinograms and planned sinograms as its own sinogram. All of these figures depict the sinograms collapsed across the entire course of treatment, but these graphical representations may also be used for single-slice comparisons as well, as depicted in FIG. 3E. While the examples depicted herein may depict cells, pixels, and/or voxels shaded in (or filled with) various intensities, opacities or transparencies, and patterns in grayscale or black-and-white, it should be understood that in other examples, cells, pixels, and/or voxels may be shaded in (or filled with) various intensities, opacities or transparencies, and patterns in one or more colors (e.g., colorized).

While the examples of sinogram bitmasks depicted in FIGS. 3A-3E depict the leaf configurations and radiation intensities for 10 binary MLC leaves and 20 gantry firing positions at three linac intensity levels, it should be understood that similar sinogram bitmasks may be generated for a system comprising a binary MLC with a different number of leaves, gantry firing positions, and linac intensity levels (e.g., a 64-leaf binary MLC, 100 gantry firing positions, linac firing at one intensity level or two intensity levels). Such sinograms may be also be generated and displayed for each patient platform position as the patient is stepped through the therapeutic radiation beam plane.

3-D Sinogram

Figure 4C:
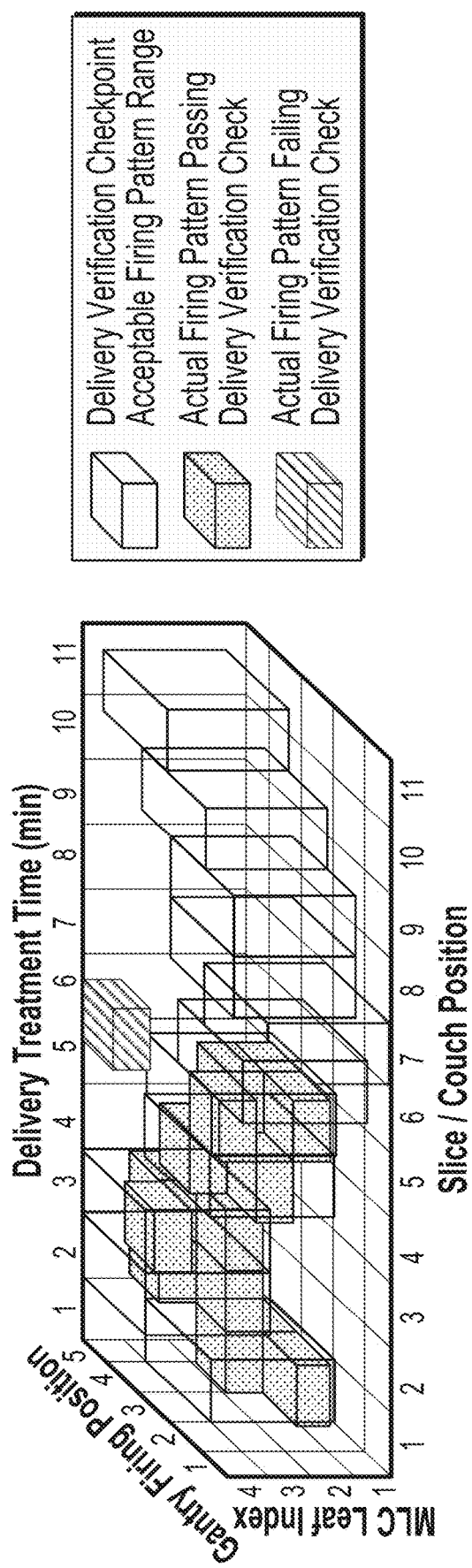
FIG. 4C depicts one example of a graphical representation comprising a 3-D bitmask or sinogram at a third time point.

Some variations of methods for monitoring radiation delivery and generating graphical representations of radiation delivery may comprise generating 3-D bitmasks or sinograms that are an extension of the bitmasks depicted in FIGS. 3A-3E. In a 3-D bitmask or sinogram, an additional axis representing patient platform position relative to the therapeutic radiation beam plane (which may be referred to as a slice or beam station or couch position or axial slide index) may be provided along with a first axis representing gantry firing position and a second axis representing MLC leaf index. By adding the third dimension of patient platform position, and/or axial slice index, and/or delivery treatment time, a radiotherapy system controller may be configured to generate a 3-D representation of the operation of the MLC leaves, rotatable gantry, and patient platform that may be compared in the same manner as the 2-D bitmask or sinogram (but comparing voxels instead of pixels). A 3-D sinogram may comprise a plurality of voxels or 3-D units where each voxel may be marked with various visually-discernible indicia (e.g., shaded or filled) to indicate with a particular MLC leaf is supposed to be opened or closed at a particular gantry firing position at a particular patient platform position relative to the therapeutic radiation beam plane. In some variations, a 3-D bitmask may be generated by generating individual 2-D bitmasks as described above for each patient platform position, and tiling (or otherwise stitching) the 2-D bitmasks of adjacent patient platforms together to form the 3-D bitmask. In some variations, the shading of each voxel may be similar to the shading described in FIGS. 3A-3E. This may help to provide a higher-dimensional slice-by-slice comparison of the treatment and would be a tube-like semi-transparent helix representing the acceptable range for the delivery verification checkpoint with opaque voxels representing measured real-time data. FIG. 4A depicts a 3-D bitmask or sinogram (for 4 MLC leaves, 5 gantry firing positions, and 11 patient platform positions) where the per-slice delivery verification checkpoint displays the firing pattern combinations that are valid (e.g., in accordance with a treatment plan and/or segmented fluence plan) and invalid (e.g., not in accordance with a treatment plan and/or segmented fluence plan) in real-time. For example, the 3-D bitmask or sinogram at time point $t_0$ depicts the MLC leaves that may be open (i.e., acceptable for them to be open as specified according to a segmented fluence map) for multiple gantry firing positions across multiple patient platform positions. FIG. 4B depicts a 3-D bitmask or sinogram at time point $t_1$ depicts the MLC leaves that have been opened for radiation delivery at patient platform positions 1-3 as voxels shaded with a second pattern, e.g., light speckles. FIG. 4C depicts a 3-D bitmask or sinogram at time point $t_1$ depicts the MLC leaves that have been opened for radiation delivery at patient platform positions 1-6 as voxels shaded with the second pattern, e.g., light speckles. MLC leaves that did not open for radiation delivery are represented by voxels that maintain the shading from time point $t_0$. An MLC leaf that opened outside of what has been specified by the segmented fluence mask (i.e., a MLC leaf opening that is not specified by the segmented fluence mask and is not one of the voxels indicated in the bitmask at time point $t_0$) may have a third and different shading pattern, e.g., hash marks. While the examples depicted herein may depict cells, pixels, and/or voxels shaded in (or filled with) various intensities, opacities or transparencies, and patterns in grayscale or black-and-white, it should be understood that in other examples, cells, pixels, and/or voxels may be shaded in (or filled with) various intensities, opacities or transparencies, and patterns in one or more colors (e.g., colorized).

While the examples of sinogram bitmasks depicted in FIGS. 4A-4C depict the leaf configurations and radiation intensities for 4 binary MLC leaves and 5 gantry firing positions for 11 patient platform positions/slices, it should be understood that similar sinogram bitmasks may be generated for a system comprising a binary MLC with a different number of leaves, gantry firing positions, and patient platform positions/slices (e.g., a 64-leaf binary MLC, 100 gantry firing positions, 20-50 patient platform positions where the distance between each patient platform position may be about 2 mm).

Pseudocolor Firing Map

For any given radiation delivery, an expected amount of firing per gantry angle may be generated by segmenting a treatment plan fluence map. A treatment plan fluence map may be segmented prior to a treatment session, for example, during treatment planning and/or treatment plan evaluation. Alternatively or additionally, some methods may comprise generating a pseudocolor firing map using MLC leaf position and/or motion sensor data, gantry position and/or motion sensor (and/or encoder) data, and radiation intensity data (e.g., acquired from a linac ionization or dose chamber and/or MV detector) over time into a single two-dimensional "heat map" of which combinations of leaf/gantry position were used most commonly to deliver radiation. This may be used to estimate how much radiation has been delivered, or conversely, how much radiation still needs to be delivered during a given treatment session. FIG. 5 depicts one variation of a pseudocolor array or representation of firing accumulation over time where each row corresponds to a gantry firing position and each column corresponds to a MLC leaf. The shading or visual indicia in each cell or pixel may represent the intensity level of radiation emitted through a particular MLC leaf at a particular gantry firing location. Alternatively or additionally, the shading or visual indicia may reflect the number of radiation pulses applied through a particular MLC leaf at a gantry firing position. At time point $t_0$, before any radiation has been emitted, the intensity level for all MLC leaves for all gantry positions may be marked as "low" intensity (or no intensity). At time point $t_1$, after radiation has been emitted from each of the five gantry firing positions, each cell may be shaded according to the intensity level applied through that leaf (e.g., low intensity, moderate intensity, high intensity, where each range may be pre-determined or specified as desirable). At time point $t_2$, after radiation has been emitted further from each of the five gantry firing positions (e.g., for multiple rotations of the gantries), the intensity level for certain MLC leaves may increase. Alternatively, a histogram of firing pattern combinations and intensity (e.g., in grayscale with varying degrees of saturation or intensity) may be generated by summing the cumulative radiation intensity applied through each MLC leaf over time.

While the examples of pseudocolor firing map depicted in FIG. 5 depict the leaf configurations and radiation intensities for 4 binary MLC leaves and 5 gantry firing positions at three intensity levels, it should be understood that similar pseudocolor firing maps may be generated for a system comprising a binary MLC with a different number of leaves, gantry firing positions, and intensity levels (e.g., a 64-leaf binary MLC, 100 gantry firing positions, linac firing at one intensity level or two intensity levels). Such pseudocolor firing maps may be also be generated and displayed for each patient platform position as the patient is stepped through the therapeutic radiation beam plane.

Gantry-Correlated Sinogram and Simulated Bore View

Figure 6B:
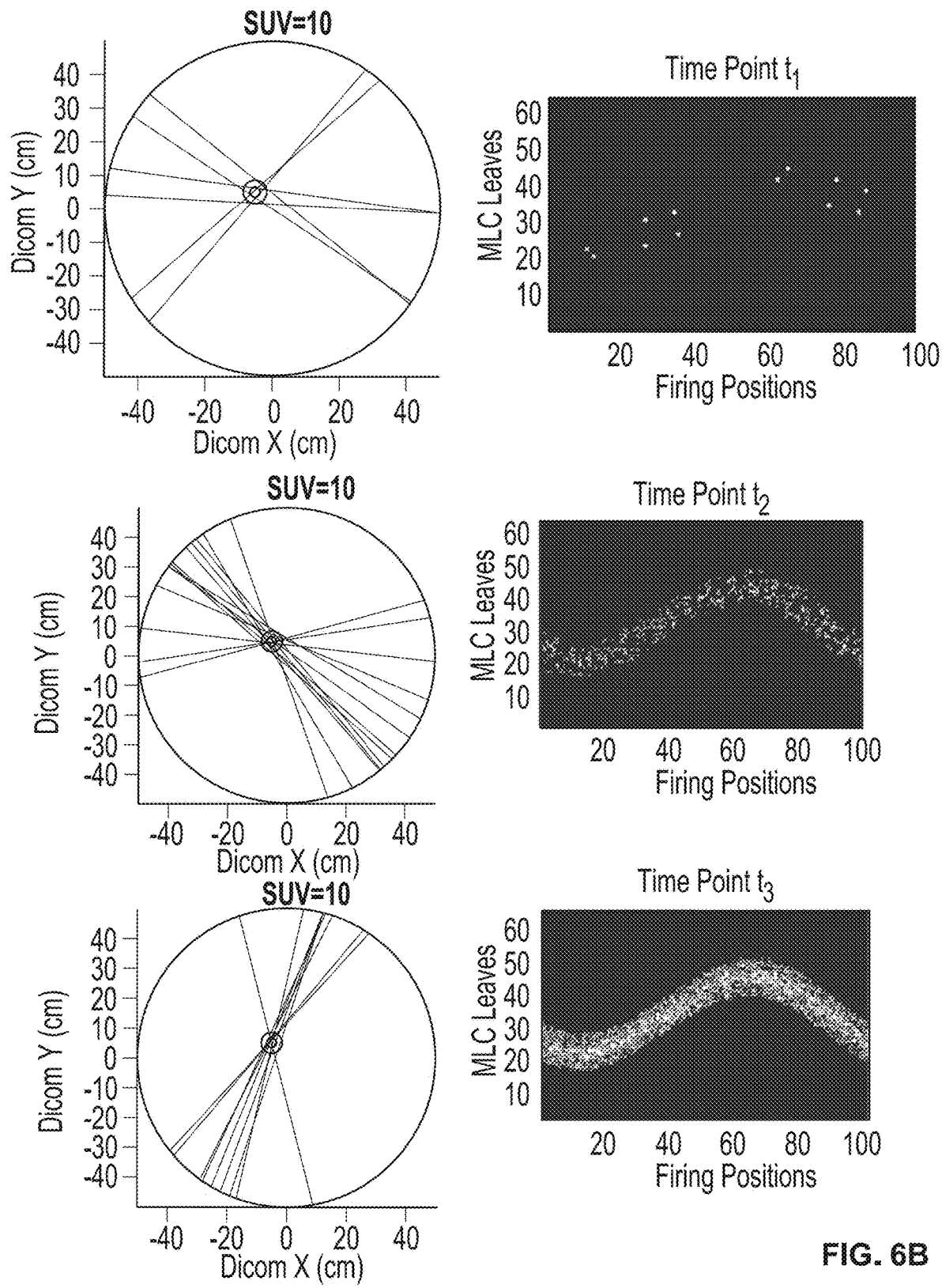
FIG. 6B depicts one example of a graphical representation comprising a beam firing interface and a cumulative treatment sinogram.

At any given point in the treatment session, the masked-out firing activity collapsed over time to a single 2D sinogram may be displayed. For example, some graphics may comprise a depiction of the active field-of-view through the longitudinal axis of a gantry bore (e.g., perpendicular to the therapeutic radiation beam plane, along an axis of rotation of the gantry) and a firing sinogram that depicts MLC leaf configuration (e.g., open or closed, in the example of a binary MLC) for each rotatable gantry firing position. In the course of treatment, the firing sinogram may represent a cumulative amount of MLC leaf activity across multiple gantry firing positions, and an active field-of-view through the longitudinal axis of a gantry bore may represent the cumulative shape of the radiation emitted to the patient. The firing sinogram may be generated using data from gantry position and/or motion sensors and MLC leaf position and/or motion sensors. FIG. 6A depicts a composite graphical representation that comprises a dose accumulation through the longitudinal axis of a gantry bore (e.g., inside a virtual bore) and a sinogram representing the cumulative MLC leaf activity over multiple gantry firing positions (for a given patient platform position or slice and/or at particular time points). Similarly, instead of displaying dose accumulation, the radiotherapy system controller may be configured to generate a graphic that may depict the beam firing on the simulated bore as depicted in FIG. 6B, where a beam firing interface (left column) is displayed alongside the overall treatment sinogram (right column).

Real-Time 4D Dose Images

Figure 7:
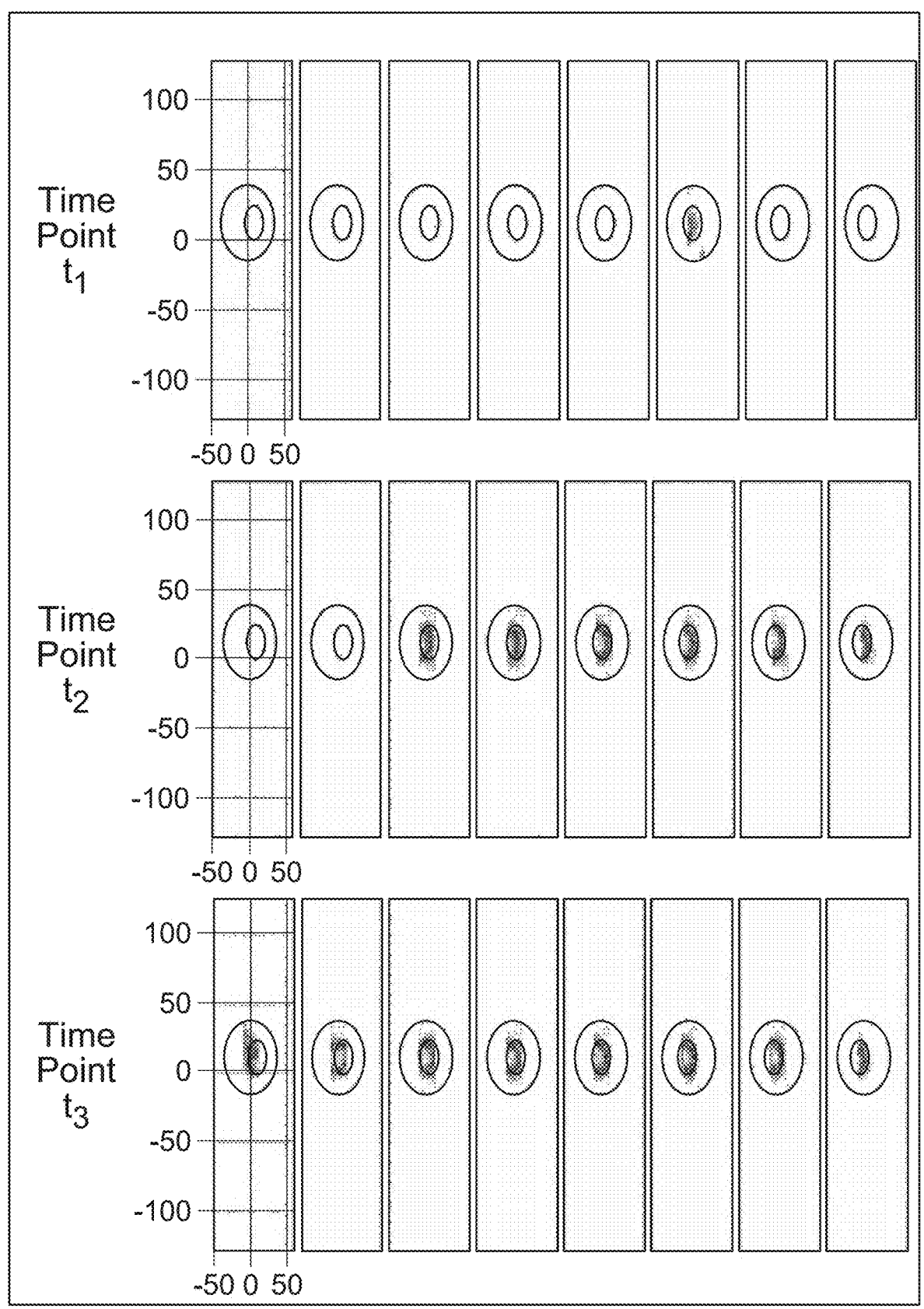
FIG. 7 depicts one example of a graphical representation comprising dose gradients that represent dose deposition across eight phases of breathing across multiple time points.

Some radiotherapy systems may be configured to obtain 4-D PET and/or CT data, and such radiotherapy systems may be configured to reconstruct the expected delivered dose grouped by the phases in which the 4-D PET and/or CT data are acquired. The radiotherapy system controller may be configured to generate a graphic that represents the delivered dose in real-time across the different breathing phases or a cinemagraphic representation of the patient anatomy, as depicted in FIG. 7, which displays dose depositions across eight phases of breathing at different time points ($t=t_1$, $t_2$, $t_3$, etc.) during the session.

Real-Time Dosimetric Objective and Plan Quality Comparisons

At any given time-point in a radiation delivery, a radiotherapy system may be configured to calculate whether or not radiation delivery is on-track to meet dosimetric objectives and plan quality indices specified by the planning system or operator. Each of these dosimetric objectives and PQIs may have their own Delivery Verification Checkpoints with acceptable ranges and tolerances, as depicted in FIG. 8A, within which the treatment plan's objectives are being achieved properly (i.e., delivery metrics meet or are within range of pre-determined criteria). FIG. 8B depicts one example where treatment plan's objectives are not being achieved properly (i.e., delivery metrics do not meet or are not within range of pre-determined criteria). The values of the various PQIs and/or dosimetric objectives may be calculated using data acquired during the treatment session, for example, data from the imaging system (e.g., imaging data and/or images from one or more of PET detectors, X-ray detectors, MRI detectors, ultrasound transducers, and/or optical cameras or imagers), and/or data from the position and/or motion sensors associated with the gantry, and/or data from the linac controller and/or ionization chamber, and/or MV detector located directly across from the linac, and/or data from the position and/or motion sensors associated with the jaws, and/or data from the position and/or motion sensors associated with the leaves of the MLC. Optionally, radiation dose delivered to the patient may be calculated using a dose calculation matrix (i.e., a matrix that maps radiation fluence values to dose values at a set of preselected regions or voxels in the patient), imaging data from the imaging system, and a radiation-firing matrix (i.e., a matrix that designates the conversion from imaging data to a fluence map) generated during treatment planning. The tolerance values may be determined by a clinician. The radiotherapy system controller may be configured to generate a notification and/or alert (which may be visual and/or audio) if one or more of the PQIs and/or dosimetric objectives are out-of-range. In some variations, if the PQIs and/or dosimetric objectives exceed high threshold or low threshold values, the radiotherapy system may be configured to halt (e.g., terminate or pause) radiation delivery.

Delivery Verification Checkpoint Interlocks

For every one of the Delivery Verification Checkpoints displayed on a graphical representation during the radiation delivery, the radiotherapy system controller may be configured to calculate the PQI values and/or dosimetric objectives to check compliance at each of the checkpoints throughout the radiation delivery treatment session. As described above, PQI values and/or dosimetric objectives may be calculated using data acquired during the treatment session, for example, data from the imaging system (e.g., imaging data and/or images from one or more of PET detectors, X-ray detectors, MRI detectors, ultrasound transducers, and/or optical cameras or imagers), and/or data from the position and/or motion sensors associated with the gantry, and/or data from the linac controller and/or ionization chamber, and/or MV detector located directly across from the linac, and/or data from the position and/or motion sensors associated with the jaws, and/or data from the position and/or motion sensors associated with the leaves of the MLC. Optionally, radiation dose delivered to the patient may be calculated using a dose calculation matrix (i.e., a matrix that maps radiation fluence values to dose values at a set of preselected regions or voxels in the patient), imaging data from the imaging system, and a radiation-firing matrix (i.e., a matrix that designates the conversion from imaging data to a fluence map) generated during treatment planning. A checkpoint may be a predetermined point in time during a treatment session, for example, an absolute time point after radiation beam-on (e.g., 5 seconds, 10 seconds, 15 seconds, etc. after beam-on), set intervals after radiation beam-on (e.g., every 10 seconds, every 20 seconds, every 30 seconds, every minute, every 5 minutes, etc.), relative time points that are proportions of the total treatment session duration (e.g., 5%, 10%, 15%, etc. of total anticipated treatment time), and/or number of linac pulses emitted (e.g., every 100 linac pulses, every 200 linac pulses, every 500 linac pulses, etc.). In some variations, a radiotherapy system controller may be configured to trigger or generate an interlock (i.e., a command to stop radiation delivery) or display other states when one or more PQI values and/or dosimetric objectives are not within an acceptable range. FIG. 9 depicts examples of interlocks or notifications of whether or not PQI values and/or dosimetric objectives have been met at various checkpoints. A checkpoint status or value of "PASSED" may indicate that one or more PQI values and/or dosimetric objectives may fall within a range or tolerance specified by the treatment plan. A checkpoint status of "FAILED" may indicate that one or more PQI values and/or dosimetric objectives may fall outside a range or tolerance specified by the treatment plan. If a checkpoint has a "FAILED" status, the radiotherapy system controller may generate a command signal for stopping radiation delivery (e.g., shutting off the therapeutic radiation source, and/or closing the MLC leaves, and/or ceasing gantry motion). In some variations, a checkpoint status or value of "WARNING" may indicate that one or more or more PQI values and/or dosimetric objectives are within, but close to the upper or lower bounds of a range or tolerance specified by the treatment plan, and/or that the number of PQI values and/or dosimetric objectives that are within range is greater than the number of PQI values and/or dosimetric objectives that are not within range. A checkpoint status or value of "WARNING" may prompt an operator to pause radiation delivery to check the functionality of certain of the radiotherapy system components. In some variations, a checkpoint status or value of "ACTIVE" may indicate that the radiotherapy system controller is in the process of determining whether the system passes or fails the checkpoint. These visual indicia may optionally be accompanied with an audible signal.

Controller

A radiotherapy system that may be configured to monitor radiation delivery during a treatment session and to generate graphical representations of radiation delivery using sensor data acquired during the treatment session may comprise a controller in communication with the imaging system of the radiotherapy system and/or the therapeutic radiation source and/or the multi-leaf collimator and/or gantry. The controller may comprise one or more processors and one or more machine-readable memories in communication with the one or more processors. The controller may be connected to a radiation treatment system and/or other systems by wired or wireless communication channels. In some variations, the controller of a radiotherapy system may be located in the same or different room as the patient. For example, the controller may be coupled to a patient platform or disposed on a trolley or medical cart adjacent to the patient and/or operator.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices may include smartphones, personal digital assistants (PDAs), cell phones, tablet PCs, phablets (personal computing devices that are larger than a smartphone, but smaller than a tablet), and the like.

Processor

In some variations, a processor may be any suitable processing device configured to run and/or execute a set of instructions or code, and may include one or more data processors, image processors, graphics processing units, digital signal processors, and/or central processing units. The processor may comprise, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

Memory

In some variations, one or more memory elements associated with the controller may include a database and may be, for example, a random access memory (RAM), a memory buffer, a hard drive, an erasable programmable read-only memory (EPROM), an electrically erasable read-only memory (EEPROM), a read-only memory (ROM), flash memory, etc. A memory may store instructions to cause the processor to execute modules, processes and/or functions associated with the system. Examples of the types of information that may be stored in a memory may include, but are not limited to, one or more treatment plans, imaging data, position and/or motion sensor data, any data associated with the calculation of fluence maps based on a treatment plan and/or clinical goals, fluence maps, segmented fluence maps comprising radiation therapy system instructions (e.g., that may direct the operation of the gantry, therapeutic radiation source, multi-leaf collimator, and/or any other components of a radiation therapy system and/or diagnostic or treatment planning system), as well as image and/or data processing instructions associated with treatment planning and/or delivery.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

A user interface may serve as a communication interface between an operator or clinician and the radiotherapy system. The user interface may comprise an input device and output device (e.g., touch screen and display) and be configured to receive input data and output data from one or more of the support arm, external magnet, sensor, delivery device, input device, output device, network, database, and server. Sensor data from one or more sensors may be received by user interface and output visually, audibly, and/or through haptic feedback by one or more output devices. As another example, operator control of an input device (e.g., joystick, keyboard, touch screen) may be received by the user interface and then processed by processor and memory for the user interface to output a control signal to one or more support arms, gantries, external magnets, intracavity devices, and delivery devices.

Some variations of a radiotherapy system may comprise a display device that may allow an operator to view graphical and/or textual representations of fluence maps, and/or dose distributions or profiles, and/or regions of interest, and/or volumes of interest, and/or patient anatomical images, and/or patient data (e.g., physiological and/or biological), and/or graphical representations of radiation delivery (as described herein), and the like. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Communication

In some embodiments, a radiotherapy system may be in communication with other computing devices via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

While various inventive variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive variations described herein. It is, therefore, to be understood that the foregoing variations are presented by way of example only and that, within the scope of the appended claims and equivalents thereto, inventive variations may be practiced otherwise than as specifically described and claimed. Inventive variations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for monitoring radiotherapy, the method comprising:
    (a) detecting acquiring PET imaging data of a target region using one or more PET detectors during the delivery of while delivering radiation for during a radiotherapy treatment session;
    (b) calculating a dosimetric objective value using the acquired PET imaging data, wherein the dosimetric objective value represents a delivered radiation dose;
    (c) comparing the dosimetric objective value with a range of acceptable dosimetric objective values for the radiotherapy treatment session; and
    (d) generating a notification that indicates whether the dosimetric objective value is within the range of acceptable dosimetric objective values.

2. The method of claim 1, further comprising pausing radiation delivery in the treatment session if the dosimetric objective value is outside the range of acceptable dosimetric objective values.

3. The method of claim 1, wherein the dosimetric objective value comprises one or more of a minimum percent volume at a selected dose level, prescription dose, maximum absolute volume at a selected dose level, and maximum percent volume at a selected dose level.

4. The method of claim 1, wherein calculating the dosimetric objective value further comprises calculating a plan quality index (PQI).

5. The method of claim 4, wherein the PQI comprises one or more of the following: mean dose levels over the target region, volumetric coverage of a 95% or 100% dose level reference over the target region, and/or a maximum dose level in an organ-at-risk (OAR).

6. The method of claim 1, wherein calculating the dosimetric objective value further comprises calculating a dose volume histogram (DVH) curve for the target region, wherein the range of acceptable dosimetric objective values is represented by bounded DVH curves comprising an upper bound curve and a lower bound curve, and comparing the dosimetric objective value with the range of acceptable dosimetric objective values comprises comparing the calculated DVH curve with the bounded DVH curves for the target region.

7. The method of claim 1, wherein (a)-(d) are performed at predetermined timepoints during the delivery of radiation.

8. The method of claim 7, wherein the predetermined timepoints are absolute timepoints during the delivery of radiation.

9. The method of claim 7, wherein the predetermined timepoints are relative timepoints that are proportions of the total treatment session duration.

10. The method of claim 7, wherein the predetermined timepoints are defined by the number of radiation pulses emitted by a therapeutic radiation source.

11. The method of claim 1, wherein generating a notification comprises displaying a checkpoint status indicator as to whether the dosimetric objective value is within the range of acceptable dosimetric objective values.

12. The method of claim 11, wherein the checkpoint status indicator displays "PASS" when the dosimetric objective value is within the range of acceptable dosimetric objective values, and the checkpoint status indicator displays "FAIL" when the dosimetric objective value is outside the range of acceptable dosimetric objective values.

13. The method of claim 2, wherein pausing radiation delivery in the treatment session further comprises generating a command signal that deactivates a therapeutic radiation source.

14. The method of claim 2, wherein pausing radiation delivery in the treatment session further comprises generating a command signal that closes at least one leaf of a multi-leaf collimator.

15. The method of claim 2, wherein pausing radiation delivery in the treatment session further comprises generating a command signal that stops gantry motion.

16. The method of claim 11, wherein comparing the dosimetric objective value with a range of acceptable dosimetric objective values further comprises updating the checkpoint status indicator to display "ACTIVE" during the comparison.

17. The method of claim 11, wherein the checkpoint status indicator displays "WARNING" when the dosimetric objective value is within a tolerance level of an upper and/or lower bounds of the range of acceptable dosimetric objective values.

* * * * *

UNITED STATES PATENT AND TRADEMARK OFFICE
CERTIFICATE OF CORRECTION

PATENT NO. : 12,303,718 B2
APPLICATION NO. : 17/479873
DATED : May 20, 2025
INVENTOR(S) : Michael Kirk Owens et al.

Page 1 of 1

It is certified that error appears in the above-identified patent and that said Letters Patent is hereby corrected as shown below:

In the Claims

At Column 33, Claim number 1, Line number 23, reads:
"(a) detecting acquiring PET imaging data of a target region using one or more PET detectors during the delivery of while delivering radiation for during a radiotherapy treatment session;"

Should read:
-- (a) detecting PET imaging data of a target region using one or more PET detectors during the delivery of radiation for a radiotherapy treatment session; --

Signed and Sealed this
Twenty-third Day of September, 2025

John A. Squires
*Director of the United States Patent and Trademark Office*